(12) United States Patent
Kroczek

(10) Patent No.: US 7,125,551 B2
(45) Date of Patent: Oct. 24, 2006

(54) METHODS FOR TREATMENT OF ASTHMATIC DISORDERS USING A MONOCLONAL ANTIBODY TO 8F4 POLYPEPTIDE

(75) Inventor: Richard Kroczek, Berlin (DE)

(73) Assignee: Bundesrepublik Deutschalnd, Berlin (DE)

(*) Notice: Subject to any disclaimer, the term of this patent is extended or adjusted under 35 U.S.C. 154(b) by 650 days.

(21) Appl. No.: 09/972,524

(22) Filed: Oct. 4, 2001

(65) Prior Publication Data

US 2002/0177191 A1    Nov. 28, 2002

Related U.S. Application Data

(63) Continuation of application No. 09/509,283, filed as application No. PCT/DE98/02896 on Sep. 23, 1998.

(30) Foreign Application Priority Data

Sep. 23, 1997  (DE)  ................ 197 41 929
May 11, 1998  (DE)  ................ 198 21 060

(51) Int. Cl.
    *A61K 39/395*   (2006.01)
    *C07K 16/00*    (2006.01)

(52) U.S. Cl. ................ 424/154.1; 424/130.1; 424/139.1; 424/141.1; 424/152.1; 424/153.1; 424/172.1; 424/173.1; 424/144.1; 530/387.1; 530/387.9; 530/388.1; 530/388.2; 530/388.22; 530/388.7; 530/388.73; 530/388.75

(58) Field of Classification Search .......... 424/130.1, 424/137.1, 139.1, 141.1, 152.1, 153.1, 154.1, 424/172.1, 173.1, 144.1; 530/388.22, 387.1, 530/387.9, 388.1, 388.2, 388.7, 382.73, 388.75
See application file for complete search history.

(56) References Cited

U.S. PATENT DOCUMENTS

2002/0164697 A1 * 11/2002 Coyle et al.

FOREIGN PATENT DOCUMENTS

| WO | WO 89/10398  | 11/1989 |
|----|--------------|---------|
| WO | WO 90/04180  | 4/1990  |
| WO | WO 98/38216  | 9/1998  |
| WO | WO 99/15553  | 4/1999  |
| WO | WO 00/46240 A | * 8/2000 |

OTHER PUBLICATIONS

Barbey et al., 1990, "DEL cell line: a "malignant histiocytosis" CD30+ t(5;6)(q35;p21) cell line." Int J Cancer. 45(3):546-53.
Buonfiglio et al., 1999, "Characterization of a novel human surface molecule selectively expressed by mature thymocytes, activated T cells and subsets of T cell lymphomas", Eur. J, Immunol. 29:2863-2874.
Buonfiglio et al., 2000, "The T cell activation molecule H4 and the CD28-like molecule ICOS are identical", Eur. J, Immunol. 30:3463-3467.
Chambers and Allison, 1997, "Co-stimulation in T cell responses." Curr Opin Immunol. 9(3):396-404. Review.
Chirgwin et al., 1979, "Isolation of biologically active ribonucleic acid from sources enriched in ribonuclease." Biochemistry. 18(24):5294-9.
Fischer et al., 1988, "A Ki-1 (CD30)-positive human cell line (Karpas 299) established from a high-grade non-Hodgkin's lymphoma, showing a 2;5 translocation and rearrangement of the T-cell receptor beta-chain gene." Blood. 72(1):234-40.
Freeman et al., 1993, "Cloning of B7-2: a CTLA-4 counter-receptor that costimulates human T cell proliferation." Science. 262(5135):909-11.
Greenfield et al., 1998, "CD28/B7 costimulation: a review", Crit. Rev. Immunol. 18:389-418.
Groettrup et al., 1996, "A third interferon-gamma-induced subunit exchange in the 20S proteasome." Eur J Immunol. 26(4):863-9.
Hara et al., 1985, Human T cell activation. II. A new activation pathway used by a major T cell population via a disulfide-bonded dimer of a 44 kilodalton polypeptide (9.3 antigen). J Exp Med. 161(6):1513-24.
Kirk et al., 1997, CTLA4-lg and anti-CD40 ligand prevent renal allograft rejection in primates. Proc Natl Acad Sci U S A. 94(16):8789-94.
Kohler and Milstein, 1975, "Continuous cultures of fused cells secreting antibody of predefined specificity." Nature. 256(5517):495-7.
Kroczek RA., 1993, "Southern and northern analysis." J Chromatogr. 618(1-2):133-45. Review.
Lani r et al., 1995, CD80 (B7) and CD86 (B70) provide similar costin lory signals for T cell proliferation, cytokine production, and g neration of CTL. J Immunol. 154(1):97-105.
Lenschow et al., 1996, "CD28/B7 system of T cell costimulation", Annu. Rev. Immunol. 14:233-258.
Linsley et al., 1992, "Coexpression and functional cooperation of CTLA-4 and CD28 on activated T lymphocytes." J Exp Med. 176(6):1595-604.
Lucas et al., 1995, "Naive CD28-deficient T cells can initiate but not sustain an in vitro antigen-specific immune response." J Immunol. 154(11):5757-68.

(Continued)

Primary Examiner—Phillip Gambel
Assistant Examiner—Ilia Ouspenski
(74) Attorney, Agent, or Firm—Jones Day

(57) ABSTRACT

The present invention relates to methods and compositions for the prevention and treatment and prevention of immune system disorders, including cancer, AIDS, asthmatic disorders, autoimmune diseases, organ transplant rejection and chronic viral diseases such as HCV or HBV infections. The therapeutic methods of the invention comprise administering molecules that modulate the activity of 8F4, thereby modulating costimulation of T cells. The present invention further provides monoclonal antibodies against the 8F4 molecule and hybridoma cells which produce said monoclonal antibodies. Pharmaceutical compositions comprising molecules that modulate the activity of 8F4 are also provided.

5 Claims, 17 Drawing Sheets

OTHER PUBLICATIONS

Nishioka et al., 1994, "The role of CD40—CD40 ligand interaction in human T cell-B cell collaboration." J Immunol. 153(3):1027-36.

Redoglia et al. 1996, "Characterization of H4: a mouse T lymphocyte activation molecule functionally associated with the CD3/T cell receptor", Eur. J. Immunol. 26:2781-2789.

Riley et al., 1997, "Intrinsic resistance to T cell infection with HIV type 1 induced by CD28 costimulation." J Immunol. 158(11):5545-53.

Schneider et al., 1982, A one-step purification of membrane proteins using a high efficiency immunomatrix. J Biol Chem. 257(18):10766-9.

Shahinian et al., 1993, "Differential T cell costimulatory requirements in CD28-deficient mice." Science. 261(5121):609-12.

Vogeli and Kaytes, 1987, "Amplification, storage, and replication of libraries." Methods Enzymol. 152:407-15.

Wallace and Miyada, 1987, "Oligonucleotide probes for the screening of recombinant DNA libraries." Methods Enzymol. 152:432-42.

Westermeier, 1997, "A Guide to Methods and Applications of DNA and Protein Separations." *Electrophoresis in Practice*, VCH Verlagsgesellschaft, Weinheim, pp. 169-181 and 224-229.

Wozney, 1990, "Using purified protein to clone its gene." Methods Enzymol. 182:738-51.

\* cited by examiner

MKSGLWYFFLFCLRIKVLTGEINGSANYEMFIFHNGGVQILCKYPDIVQQFKMQLL
KGGQILCDLTKTKGSGNTVSIKSLKFCHSQLSNNSVSFFLYNLDHSHANYYFCNLSI
FDPPPFKVTLTGGYLHIYESQLCCQLKFWLPIGCAAFVVVCILGCILICWLTKKKYS
SSVHDPNGEYMFMRAVNTAKKSRLTDVTL

FIG. 15

```
CGAGAGCCTGAATTCACTGTCAGCTTTGAACACTGAACGCGAGGACTGTTAACTGTTTCT
GGCAAACATGAAGTCAGGCCTCTGGTATTTCTTTCTCTTCTGCTTGCGCATTAAAGTTTT
AACAGGAGAAATCAATGGTTCTGCCAATTATGAGATGTTTATATTTCACAACGGAGGTGT
ACAAATTTATGCAAATATCCTGACATTGTCCAGCAATTTAAAATGCAGTTGCTGAAAGG
GGGGCAAATACTCTGCGATCTCACTAAGACAAAAGGAAGTGGAAACACAGTGTCCATTAA
GAGTCTGAAATTCTGCCATTCTCAGTTATCCAACAACAGTGTCTCTTTTTTCTATACAA
CTTGGACCATTCTCATGCCAACTATTACTTCTGCAACCTATCAATTTTGATCCTCCTCC
TTTTAAAGTAACTCTTACAGGAGGATATTTGCATATTTATGAATCACAACTTTGTTGCCA
GCTGAAGTTCTGGTTACCCATAGGATGTGCAGCCTTTGTTGTAGTCTGCATTTTGGGATG
CATACTTATTTGTTGGCTTACAAAAAGAAGTATTCATCCAGTGTGCACGACCCTAACGG
TGAATACATGTTCATGAGAGCAGTGAACACAGCCAAAAAATCTAGACTCACAGATGTGAC
CCTATAATATGGAACTCTGGCACCCAGGCATGAAGCACGTTGGCCAGTTTTCCTCAACTT
GAAGTGCAAGATTCTCTTATTTCCGGGACCACGGAGAGTCTGACTTAACTACATACATCT
TCTGCTGGTGTTTTGTTCAATCTGGAAGAATGACTGTATCAGTCAATGGGGATTTTAACA
GACTGCCTTGGTACTGCCGAGTCCTCTCAAAACAAACACCCTCTTGCAACCAGCTTTGGA
GAAAGCCCAGCTCCTGTGTGCTCACTGGGAGTGGAATCCCTGTCTCCACATCTGCTCCTA
GCAGTGCATCAGCCAGTAAACAAACACATTTACAAGAAAAATGTTTAAAGATGCCAGG
GGTACTGAATCTGCAAAGCAAATGAGCAGCCAAGGACCAGCATCTGTCCGCATTTCACTA
TCATACTACCTCTTCTTTCTGTAGGGATGAGAATTCCTCTTTAATCAGTCAAGGGAGAT
GCTTCAAAGCTGGAGCTATTTTATTTCTGAGATGTTGATGTGAACTGTACATTAGTACAT
ACTCAGTACTCTCCTTCAATTGCTGAACCCCAGTTGACCATTTTACCAAGACTTTAGATG
CTTTCTTGTGCCCTCAATTTTCTTTTAAAAATACTTCTACATGACTGCTTGACAGCCCA
ACAGCCACTCTCAATAGAGAGCTATGTCTTACATTCTTTCCTCTGCTGCTCAATAGTTTT
ATATATCTATGCATACATATATACACACATATGTATATAAAATTCATAATGAATATATTT
GCCTATATTCTCCCTACAAGAATATTTTGCTCCAGAAAGACATGTTCTTTCTCAAATT
CAGTTAAAATGGTTTACTTTGTTCAAGTTAGTGGTAGGAAACATTGCCCGGAATTGAAAG
CAAATTTATTTTATTATCCTATTTTCTACCATTATCTATGTTTTCATGGTGCTATTAATT
ACAAGTTTAGTTCTTTTGTAGATCATATTAAAATTGCAAACAAAATCATCTTTAATGGG
CCAGCATTCTCATGGGGTAGAGCAGAATATTCATTTAGCCTGAAAGCTGCAGTTACTATA
GGTTGCTGTCAGACTATACCCATGGTGCCTCTGGGCTTGACAGGTCAAAATGGTCCCCAT
CAGCCTGGAGCAGCCCTCCAGACCTGGGTGGAATTCCAGGGTTGAGAGACTCCCCTGAGC
CAGAGGCCACTAGGTATTCTTGCTCCCAGAGGCTGAAGTCACCCTGGGAATCACAGTGGT
CTACCTGCATTCATAATTCCAGGATCTGTGAAGAGCACATATGTGTCAGGGCACAATTCC
CTCTCATAAAAACCACACAGCCTGGAAATTGGCCCTGGCCCTTCAAGATAGCCTTCTTTA
GAATATGATTTGGCTAGAAAGATTCTTAAATATGTGGAATATGATTATTCTTAGCTGGAA
TATTTTCTCTACTTCCTGTCTGCATGCCCAAGGCTTCTGAAGCAGCCAATGTCGATGCAA
CAACATTTGTAACTTTAGGTAAACTGGGATTATGTTGTAGTTTAACATTTTGTAACTGTG
TGCTTATAGTTTACAAGTGAGACCCGATATGTCATTATGCATACTTATATTATCTTAAGC
ATGTGTAATGCTGGATGTGTACAGTACAGTACTGAACTTGTAATTTGAATCTAGTATGGT
GTTCTGTTTTCAGCTGACTTGGACAACCTGACTGGCTTTGCACAGGTGTTCCCTGAGTTG
TTTGCAGGTTTCTGTGTGTGGGGTGGGGTATGGGGAGGAGAACCTTCATGGTGGCCCACC
TGGCCTGGTTGTCCAAGCTGTGCCTCGACACATCCTCATCCCCAGCATGGGACACCTCAA
GATGAATAATAATTCACAAAATTTCTGTGAAATCAAATCCAGTTTTAAGAGGAGCCACTT
ATCAAAGAGATTTTAACAGTAGTAAGAAGGCAAAGAATAAACATTTGATATTCAGCAACT
G
```

FIG. 16

METHODS FOR TREATMENT OF ASTHMATIC DISORDERS USING A MONOCLONAL ANTIBODY TO 8F4 POLYPEPTIDE

CROSS REFERENCE TO RELATED APPLICATIONS

This application claims priority to U.S. patent application Ser. No. 09/509,283, filed Aug. 11, 2000, which claims priority to PCT Application PCT/DE98/02896, filed Sep. 23, 1998, and German Applications DE 19821060.4, filed May 11, 1998, and DE 19741929.1, filed Sep. 23, 1997, each of which is incorporated herein by reference in its entirety.

BACKGROUND OF THE INVENTION

The invention relates to a polypeptide (8F4 molecule) having the biological activity of costimulating T cells. The invention further relates to monoclonal antibodies against the 8F4 molecule and hybridoma cells which produce the monoclonal antibodies. T5he invention additionally relates to the use of substances which inhibit the biological activity of the polypeptide 8F4 according to the invention, in particular monoclonal antibodies, natural or synthetic ligands, agonists or antagonists, as pharmaceuticals. In particular, the invention relates to the use of these substances for the prevention or therapy of disorders in which the immune system is involved, in particular for the treatment of autoimmune diseases and for the prevention of rejection reactions with organ transplants. The invention additionally relates to the use of the 8F4 molecule or of cells which contain the 8F4 molecule as pharmaceuticals, in particular for the prevention or therapy of disorders in which the immune system is involved, in particular for the treatment of cancers, Aids, asthmatic disorders or chronic viral diseases such as HCV or HBV infections. The invention further relates to the use of substances which specifically recognize the polypeptide according to the invention, in particular monoclonal antibodies, natural or synthetic ligands, agonists or antagonists, for the diagnosis of disorders in which the immune system is involved. In particular, the invention relates to diagnosis by means of an ELISA detection, a flow cytometry or a Western blot, a radioimmunological detection, a nephelometry or a histochemical staining.

T lymphocytes recognize their antigen, which is presented by "antigen-presenting cells", for example dendritic cells, B cells and macrophages, through their T-cell receptor. Recognition of the antigen by the T-Cell receptor alone is, however, in most cases insufficient for adequate activation of T lymphocytes. The latter makes additional simultaneous stimulation (also called "costimulation" hereinafter) by other receptor molecules on the surface of the T lymphocytes necessary. One of these receptor molecules is the so-called CD28 receptor which is stimulated by the costimulating molecule B7. If these "costimulatory" molecules, for example CD28, are effective, then the activation of the T cell reaches an adequate level after recognition of the antigen by the T-cell receptor. After such a complete activation, the T cell expresses additional molecules, for example CD25, CD69, CD71, on the surface and synthesizes numerous cytokines, for example IL-2 and IFN-γ, which function as messengers. Both these additional surface molecules and the cytokines serve for the T cell to exchange information with other cells in the immune system. The activated T cells direct the entire antigen-specific immune defenses through the additional surface molecules and the cytokines. Both the generation of cytotoxic cells ("killer cells") and the generation of antigen-specific antibodies by B cells is controlled in this way. Cytotoxic cells, as well as the specifically formed antibodies, eliminate viral or bacterial pathogens which enter the body. In some cases, however, the immune response goes too far, and the immune system is directed against the body's own cells. This leads to the occurrence of "autoimmune diseases", for example to rheumatoid arthritis, ankylosing spondylitis, Sjögren's syndrome, ulcerative colitis inter alia. One of the essential sites of cooperation between antigen-activated T cells and other cells of the immune system are the secondary lymphatic organs, including the tonsils. This is where the T lymphocytes are activated by the antigen presented by dendritic cells, and this is where T lymphocytes interact with B cells. Through this interaction, B cells secrete, after several intermediate stages of differentiation, antigen-specific antibodies of the IgM and IgG types.

The costimulatory molecule which has been characterized best and is among the most effective to date is the CD28 surface molecule (called CD28 receptor or CD28 hereinafter) which is constitutively expressed on a large fraction of T cells. Costimulation by CD28 in vitro leads, after recognition of the antigen by the T-cell receptor, to a very large increase in cytokine secretion, for example of IL-2 and IFN-γ, and to a marked up-regulation of the expression of cell surface molecules such as CD25, CD69, CD71, which are necessary for interaction of T cells with other immune cells, for example B lymphocytes; cf. Chambers and Allison, *Current Opinion in Immunology* 9 (1997), 396–404. Costimulation via the CD28 receptor can also markedly increase the proliferation of T lymphocytes. In addition, costimulation via the CD28 receptor optimizes the T-cell control of B-lymphocyte function so that there is increased secretion of antibodies.

If the function of the CD28 receptor is abolished, there is a drastic loss of function in the immune defenses. This has been shown by means of a transgenic mouse in which the CD28 gene was destroyed by homologous recombination (a so-called "CD28 knock-out"). The destruction in this way of activation of the antigen-specific T cells leads to lack of costimulation. This in turn leads to a disturbance of T-cell function, that is to say to a reduced proliferation of T cells and to a drastically reduced synthesis of various cytokines. The lack of costimulation eventually leads to a reduced function of the antigen-specific immune defenses. Thus, inter alia, the formation of antigen-specific IgG1 and IgG2 antibodies by B lymphocytes is reduced to 10% of the normal level through the lack of CD28; cf. Shahinian et al., *Science* 262 (1993), 609–612; Lucas et al. Journal of *Immunology* 154 (1995), 5757–5768. It is also possible in vitro to prevent the Aids virus entering T lymphocytes by costimulation by CD28; cf. Riley et al., *Journal of Immunology* 158 (1997), 5545–5553. Corresponding experiments in vivo have not yet been carried out. It is known that CD28 switches on many cytokine genes which may lead to considerable side effects in vivo. Blockade of CD28 receptors by a soluble CTLA-4 immunoglobulin molecule has been employed successfully in a monkey model to prevent the rejection of transplanted kidneys. In this case, CTLA-4 had been employed in combination with an antibody against the CD40 ligand molecule; cf. Kirk et al., *Proc. Natl. Acad. Sci. USA* 94 (1997) 8789–8794. However, blockade of CD28 receptors affects all T lymphocytes and not just those already activated because CD28 is constitutively expressed on T lymphocytes.

SUMMARY OF THE INVENTION

There is thus a need for a costimulating surface molecule which is expressed only on activated T lymphocytes. The invention is therefore based on the object of providing a surface molecule on activated T cells which has a strong costimulatory effect on central functions of T lymphocytes. Another object of the invention is to provide substances, for example monoclonal antibodies against the costimulatory surface molecule, natural or synthetic ligands, agonists or antagonists of the surface molecule.

In a first embodiment, the invention relates to a polypeptide having the biological activity of costimulation of T cells, characterized in that a) the polypeptide occurs on activated $CD4^+$ and $CD8^+$ T lymphocytes but not on resting or activated B cells, granulocytes, monocytes, NK cells (natural killer cells) or dendritic cells, and b) the polypeptide is a dimer, the polypeptide having a molecular weight of about 55 to 60 kDa (kilodalton) determined in a non-reducing sodium dodecyl sulphate polyacrylamide gel electrophoresis (SDS-PAGE), and the two polypeptide chains of the polypeptide having a molecular weight of about 27 kDa and about 29 kDa measured in a reducing SDS-PAGE.

The polypeptide according to the invention (also called 8F4 molecule or 8F4 hereinafter) is expressed only after activation of the T lymphocytes, specifically both on $CD4^+$ and on $CD8^+$ T cells. In a non-reducing SDS-PAGE, the 8F4 molecule has a molecular weight between about 55 and 60 kDa (kilodalton). The 8F4 molecule is composed of two peptide chains, and the two peptide chains have a molecular weight of about 27 and about 29 kDa in a reducing SDS-PAGE. The 8F4 antigen can be unambiguously detected histologically on activated T lymphocytes in the lymphatic tissue of the tonsils and lymph nodes, especially in the germinal centres, the site of interaction of T lymphocytes and B lymphocytes in the generation of antibodies. Tonsillar T cells isolated ex vivo are about 50–80% positive for the 8F4 antigen and show signs of advanced activation. The 8F4 molecule is not detectable on resting or activated B cells, granulocytes, monocytes, NK cells and dendritic cells.

An important biological activity of the 8F4 molecule is its costimulating activity on T lymphocytes. The costimulating activity can be determined by the method of Linsley et al., *Journal of Experimental Medicine* 176 (1992), 1595–604. The costimulating activity of the 8F4 molecule resembles the costimulating activity of the CD28 molecule, which has been identified as the central enhancement element of antigen recognition by the immune system. The 8F4 molecule differs in many aspects from CD28, however. Thus, expression of the 8F4 molecule on the surface of the T cells requires induction, whereas CD28 is constitutively expressed. There are also distinct differences detectable in the function: costimulation by CD28 leads to overexpression of numerous lymphokines, inter alia of interleukin-2 (IL-2). Costimulation by 8F4 also leads to enhanced secretion of lymphokines, but not of IL-2. The costimulatory activity of the 8F4 molecule thus differs from the activity of the CD28 molecule. Since stimulation by 8F4 does not switch on all cytokine genes, costimulation by 8F4 in vivo is advantageous, for example compared with costimulation via the CD28 receptor. Moreover, the induction, the expression, the site of expression and the function of the 8F4 molecule differ from all other known molecules with costimulatory activity.

The 8F4 molecule according to the invention is a novel surface molecule on activated T cells which has a strong costimulatory effect on central functions of T lymphocytes. Expression in vivo indicates inter alia an essential involvement of the 8F4 molecule in the cooperation of T cells with other cells of the immune system such as B cells or dendritic cells within the humoral and cellular immune defenses against viruses and bacteria.

After expression, the 8F4 molecule has in vitro a strong costimulatory effect on various functions of T lymphocytes:
1. Marked enhancement of the proliferation of T lymphocytes.
2. Marked enhancement of the synthesis of certain cytokines by T lymphocytes.
3. Greatly increased expression of control molecules, for example surface molecules and cytokines, on and in T lymphocytes.
4. Marked improvement in T-cell-induced antibody formation (IgM and IgG) by B cells.

The present invention furthermore provides a polypeptide having the biological activity of costimulation of T cells and having an amino acid sequence which shows at least 40% homology with the sequence comprising 199 amino acids in FIG. 15 (SEQ ID NO:2), or a biologically active fragment or an analogue thereof. A biologically active fragment or analogue is a fragment or analogue which likewise shows a costimulatory effect on T-cell lymphocytes or at least displays a biological effect of the nature of a blockage. Preference is given to a polypeptide or a biologically active fragment or analogue thereof which shows at least 60% homology with the sequence comprising 199 amino acids in FIG. 15 (SEQ ID NO:2). In a particularly preferred embodiment, the polypeptide according to the invention comprises an amino acid sequence which shows at least 80% homology with the sequence comprising 199 amino acids in FIG. 15 (SEQ ID NO:2), or a biologically active fragment or analogue thereof.

A particularly preferred polypeptide has the biological activity of costimulation of T cells and comprises an amino acid sequence as shown in FIG. 15 (SEQ ID NO:2), or a biologically active fragment or an analogue thereof.

The invention includes allelic variants, fragments and analogues of the 8F4 molecule. These variants include naturally occurring allelic variants, substitution analogues in which one or more amino acids have been substituted by different amino acids, substitution analogues in which one or more amino acids have been substituted by different amino acids, deletion analogues in which one or more amino acids have been deleted and addition analogues in which one or more amino acids have been added. Deletion and addition of one or more amino acids may be done either at an internal region of the polypeptide or at the amino or carboxyl terminus.

Polypeptides according to the invention fused to heterologous polypeptides are likewise embraced.

In another embodiment, the invention relates to DNA sequences which encode a polypeptide according to the invention or a biologically active fragment or analogue thereof.

These DNA sequences include the sequence shown in SEQ ID NO:1 (FIG. 16) as well as allelic variants, fragments, and analogues having biological activity.

A preferred DNA sequence encodes a polypeptide having the biological activity of costimulation of T cells, the sequence being selected from the group consisting of:
  a) the DNA sequence shown in SEQ ID NO:1 (FIG. 16) and its complementary strand
  b) DNA sequence hybridizing with the sequences in (a) and
  c) DNA sequences which, because of the degeneracy of the genetic code, hybridize with the sequences in (a)

and (b). The aforementioned DNA sequences preferably hybridize together under stringent conditions.

Also provided are vectors which comprise these DNA sequences, and host cells which are transformed or transfected with these vectors.

In another embodiment, the invention relates to monoclonal antibodies against the 8F4 molecule. The monoclonal antibodies according to the invention can be prepared in a conventional way by the method described by Milstein and Kohler, Nature 256 (1975), 495–497. In particular, the monoclonal antibodies according to the invention can be prepared by immunizing mice with T cells which have been activated in vitro with phorbol myristate acetate (PMA) and ionomycin ("2-signal system") for 24 h. The spleen cells of the immunized mice are fused with myeloma cells. 8F4-specific monoclonal antibodies are identified by their recognition of 2-signal-activated but not resting T lymphocytes. Moreover 8F4-specific antibodies do not stain T cells stimulated with one signal (either PMA or ionomycin) in a detection method carried out in a conventional way. 8F4-specific antibodies produce a typical staining pattern of tonsillar T cells and recognize an antigen of about 55 to 60 kDa in a non-reducing SDS-PAGE and of about 27 kDa and about 29 kDa in a reducing SDS-PAGE on activated T lymphocytes.

In another embodiment, the invention relates to hybridoma cells which produce the monoclonal antibodies according to the invention.

In another embodiment, the invention relates to the use of substances which inhibit the biological activity of the polypeptide 8F4 according to the invention as pharmaceuticals. The use of the monoclonal antibodies according to the invention, natural or synthetic ligands, agonists or antagonists of the 8F4 molecule is particularly preferred. These substances can be used as pharmaceuticals for the prevention or therapy of disorders in which the immune system is involved, in particular for the treatment or autoimmune diseases or for prevention of rejection reactions in organ transplants. Blockade of the interaction of the 8F4 antigen with its receptor improves, for example, the prevention of organ rejection because such a blockade affects only previously activated T lymphocytes. Another embodiment of the invention relates to the use of the polypeptide according to the invention as pharmaceutical. The polypeptide according to the invention can be used in particular for the prevention or therapy of disorders in which the immune system is involved, in particular for the treatment of cancers, AIDS, asthmatic disorders or chronic viral diseases such as HCV or HBV infections.

The polypeptide according to the invention can likewise be introduced into cells in a conventional way so that these cells for example constitutively express the polypeptide. For example, the nucleic acid sequence encoding the polypeptide or a vector comprising the nucleic acid sequencing encoding the polypeptide, for example the cDNA or genomic DNA, promoters, enhancers and other elements required for expression of the nucleic acid sequence can be inserted into a cell. The 8F4 cDNA (2641 nucleotides) depicted in FIG. 16 (SEQ ID NO:1) or fragments or derivatives thereof, is preferably employed for expression of the polypeptide according to the invention or fragments thereof.

The polypeptide according to the invention can also be introduced for example by means of liposomes into cells which then form the polypeptide on their cell surface. These cells can be used as pharmaceuticals according to the invention, in particular for restoring correct regulation of the human immune system, as occurs within the framework of numerous chronic infectious diseases, for example within the framework of AIDS, asthmatic disorders or in chronic viral hepatitis (for example HCV, HBV), or for stimulating the immune system in vitro or in vivo such as, for example, be used for the therapy of cancers.

In another embodiment, substances which specifically recognize the polypeptide according to the invention are used for diagnosing disorders in which the immune system is involved, the substances embracing in particular a monoclonal antibody, natural or synthetic ligands, agonists or antagonists. It is possible to use for the diagnosis for example an ELISA detection, flow cytometry, Western blot, radioimmunoassay, nephelometry or a histochemical staining. The substances which recognize the polypeptide according to the invention also comprise nucleic acid sequences, the latter preferably being employed for hybridization and/or nucleic acid (RNA, DNA) amplification (for example PCR).

In another embodiment, the invention relates to substances which have a positive or negative effect on (modulate) the signal transduction pathway of the polypeptide according to the invention into the T cell, and to the use of these substances as pharmaceuticals.

In another embodiment, the invention relates to substances which prevent up-regulation of the polypeptide according to the invention on the T-cell surface, and to the use thereof as pharmaceuticals.

In another embodiment, the polypeptide according to the invention or fragments thereof is expressed by a transgenic animal.

In another embodiment, the invention embraces a transgenic animal in which the gene which codes for the polypeptide according to the invention has been switched off ("knock-out").

"bioPE" means biotinylated antibody and streptavidin-phycoerythrin secondary reagent.

Figure 6:
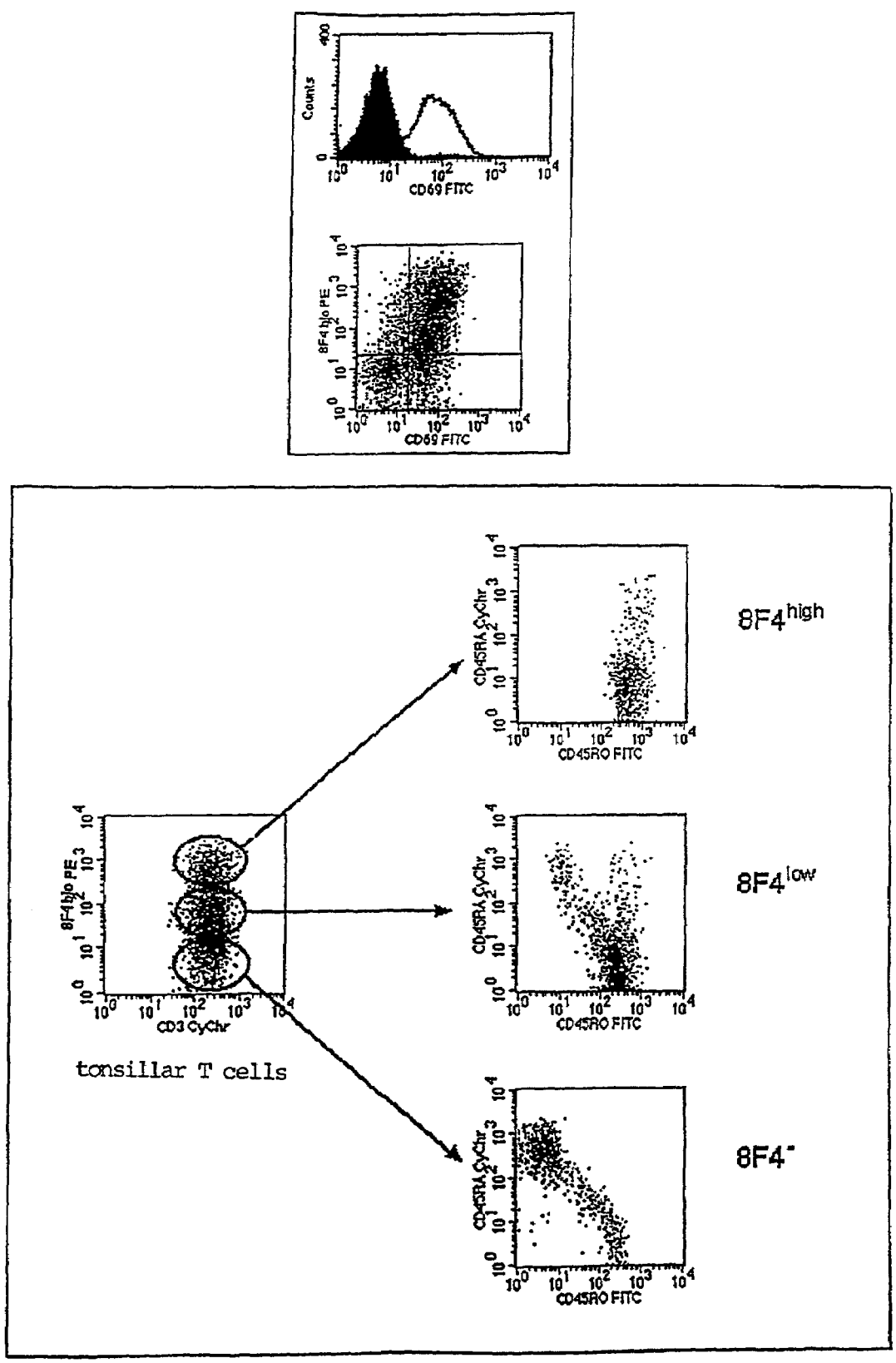

FIG. 6 shows the coexpression of the 8F4 molecule with other activation markers (CD69, CD45) in a flow cytometry.

Figure 7:
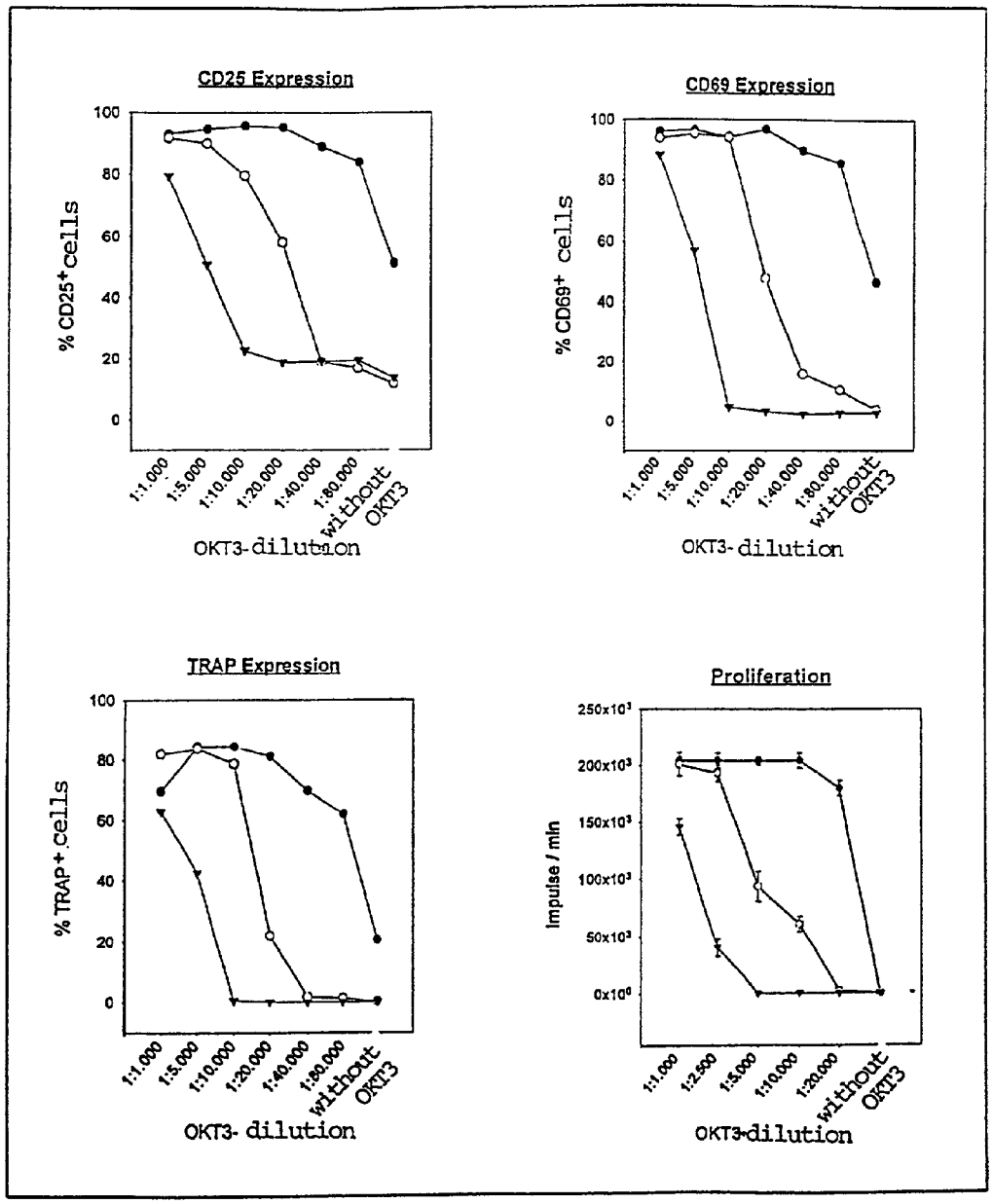

FIG. 7 shows diagrammatically the enhanced expression of activation molecules on T lymphocytes after costimulation by 8F4. Open circles (○) represent 8F4 antibodies; triangles (◆) represent nonspecific antibodies of the same isotype; filled circles (●) represent anti-CD28 antibodies-9.3.

Figure 8:
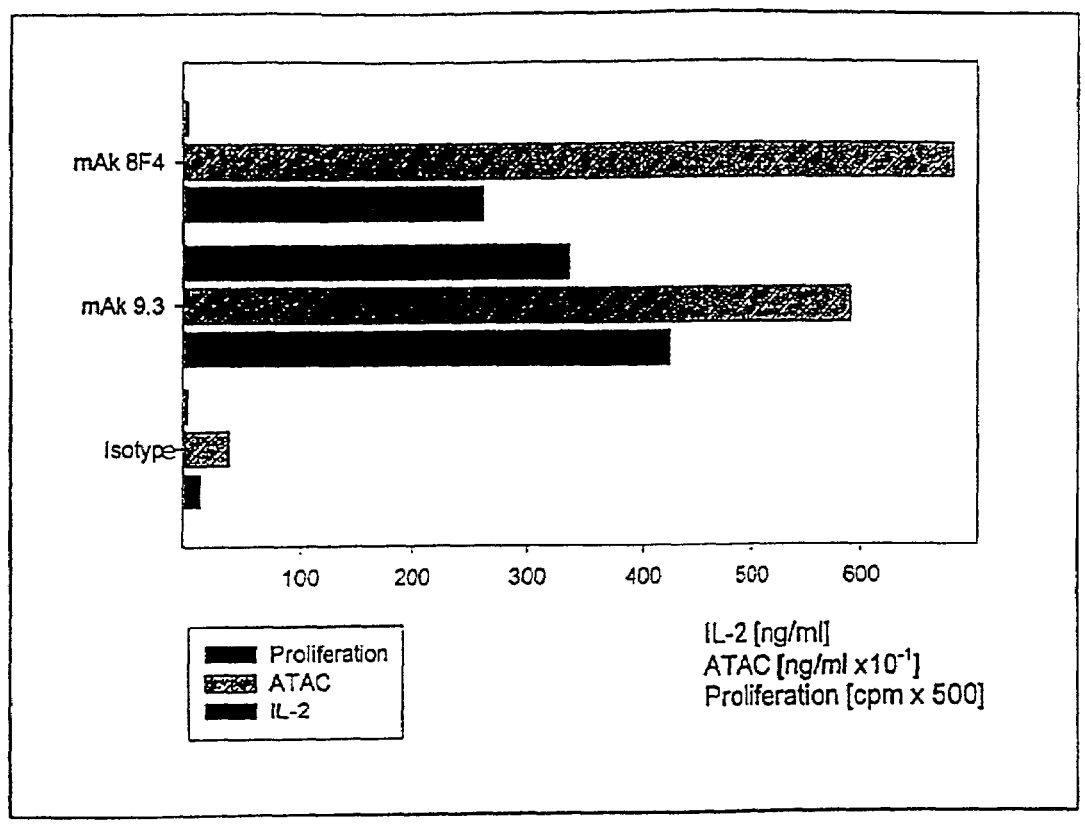

FIG. 8 shows a diagrammatic comparison of the costimulating effect of 8F4 with the costimulating effect of CD28. "mAk" means monoclonal antibodies; "ATAC" means "activation induced T-cell-derived and chemokine-related"; "cpm" means radioactive disintegrations per minute.

Figure 9:
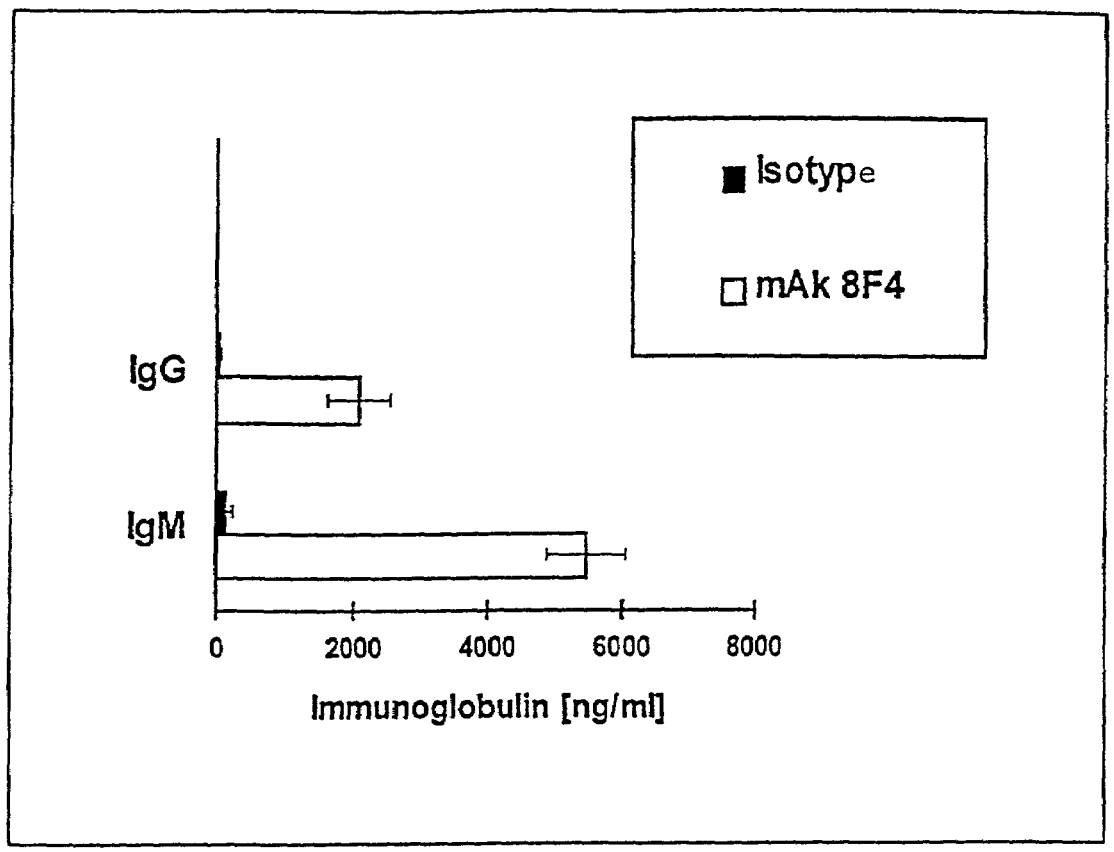

FIG. 9 shows diagrammatically the enhancement of the synthesis of the antibodies of the IgM and IgG types by B cells after costimulation of T cells. "ng" means nanogram; "ml" means milliliter; "mAk" means monoclonal antibody.

Figure 10:
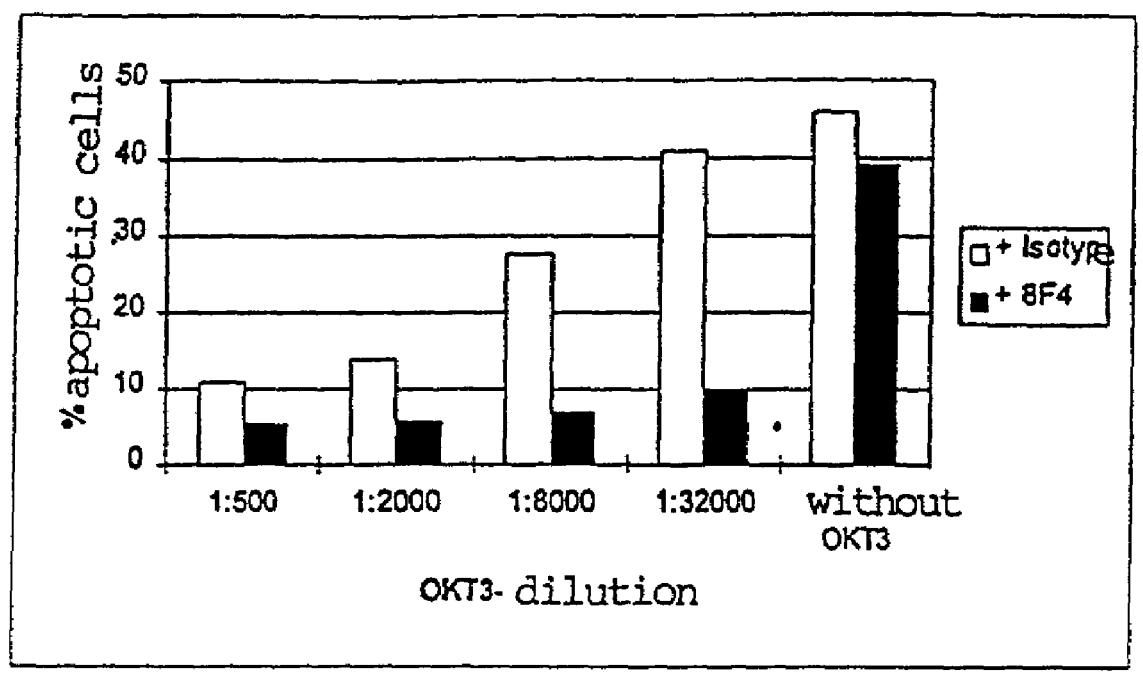

FIG. 10 shows diagrammatically the prevention of the activation-induced apoptosis of peripheral T cells after costimulation by 8F4.

Figure 11:
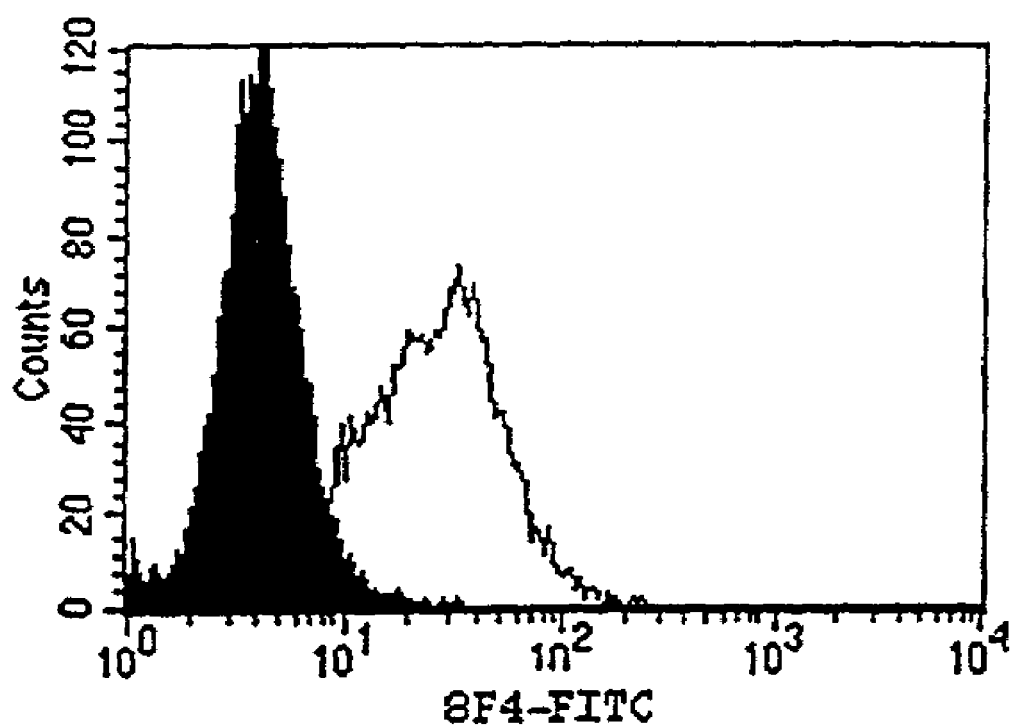

FIG. 11 shows expression of the 8F4 antigen on the MOLT-4V cell line. MOLT-4V cells were stained with a fluorescein-labelled 8F4 antibody (8F4-FITC) and investigated in flow cytometry (unfilled line, comparing with an isotype control (filled line)).

Figure 1:
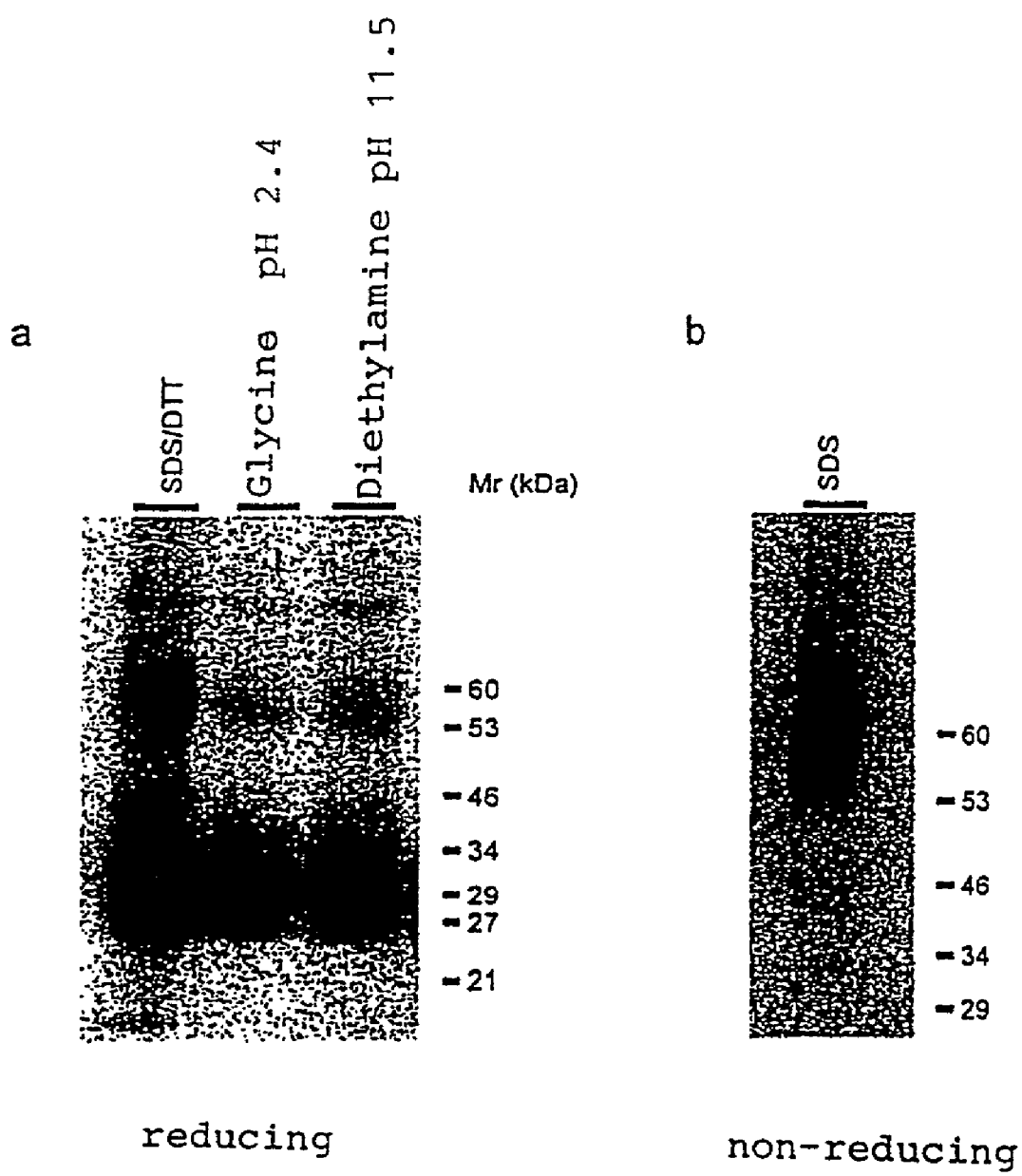
FIG. 1 shows the result of an immunoprecipitation of the 8F4 antigen from activated human T cells. (a) Sodium dodecyl sulphate polyacrylamide gel electrophoresis (SDS-PAGE; 12% polyacrylamide gel (PAA gel)) reducing, (b) SDS-PAGE (10% PAA gel) non-reducing. The conditions for elution of the antigen from the 8F4 matrix are indicated. "SDS" means sodium dodecyl sulphate; "DTT" means dithiothreitol, "Mr" means molecular weight and "kDa" means kilodaltons.
Figure 2A:
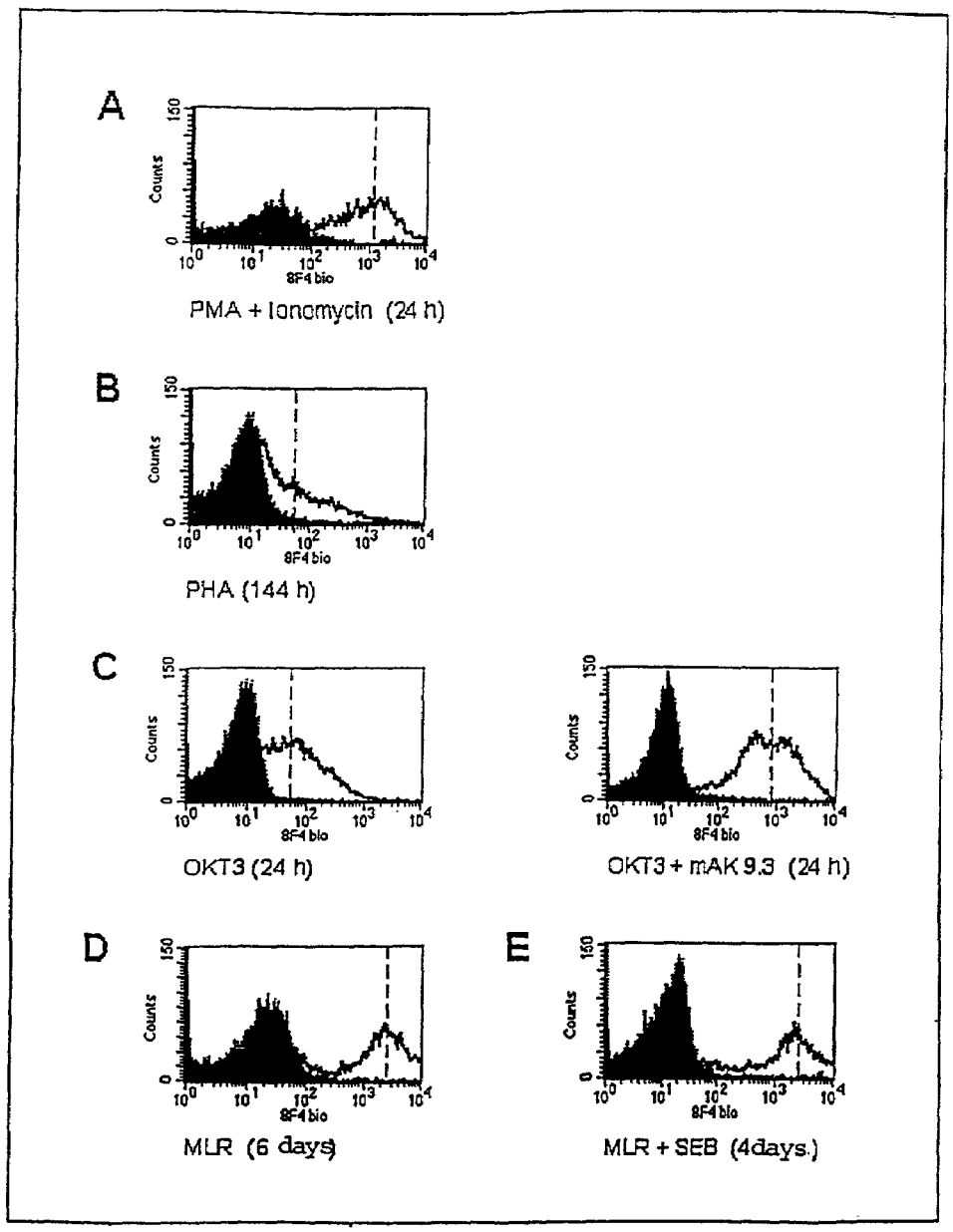
FIG. 2a shows the result of a flow cytometry after induction of the 8F4 antigen on CD4$^+$ T cells. The activation time for the T cells is indicated in parentheses. "PMA" means phorbol myristate acetate; "PHA" means phytohaemagglutinin; "OKT3" is a monoclonal antibody against CD3; "MLR" means mixed lymphocyte reaction; "mAK 9.3" is a monoclonal antibody against CD28; "SEB" means staphylococcal enterotoxin B.
Figure 2B:
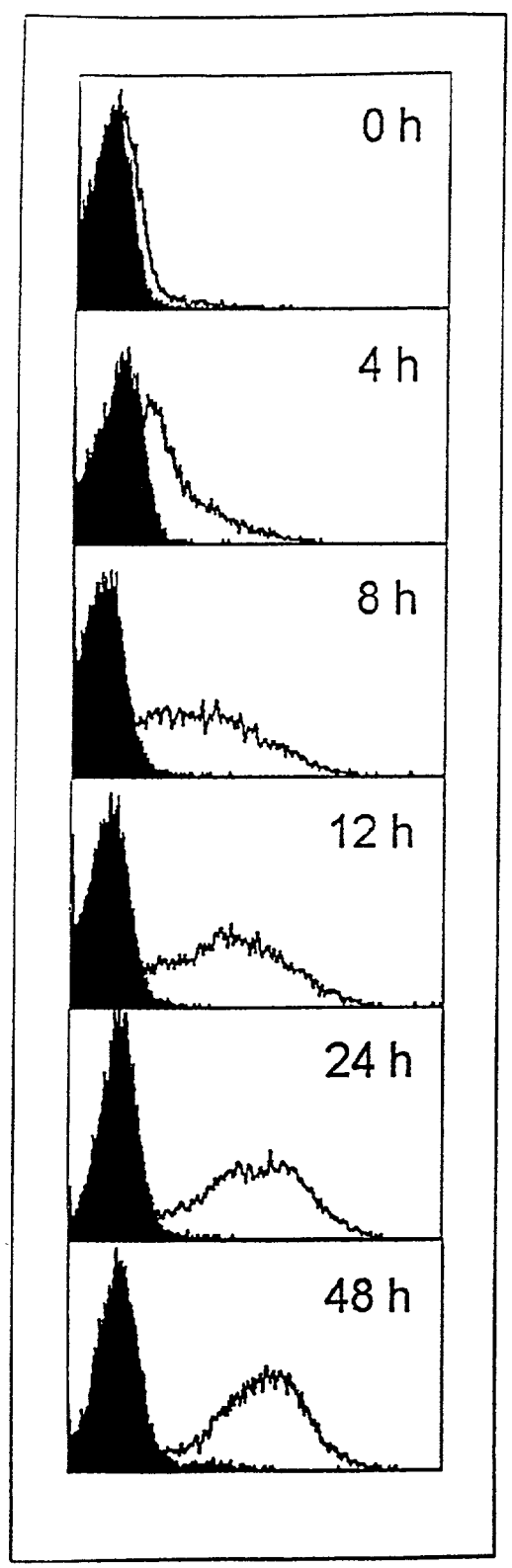
FIG. 2b shows the result for the kinetics of induction of the 8F4 antigen on CD4$^+$ T cells after activation with PMA and ionomycin in a flow cytometry. The immunofluorescence (log) is plotted against the cell count.
Figure 3:
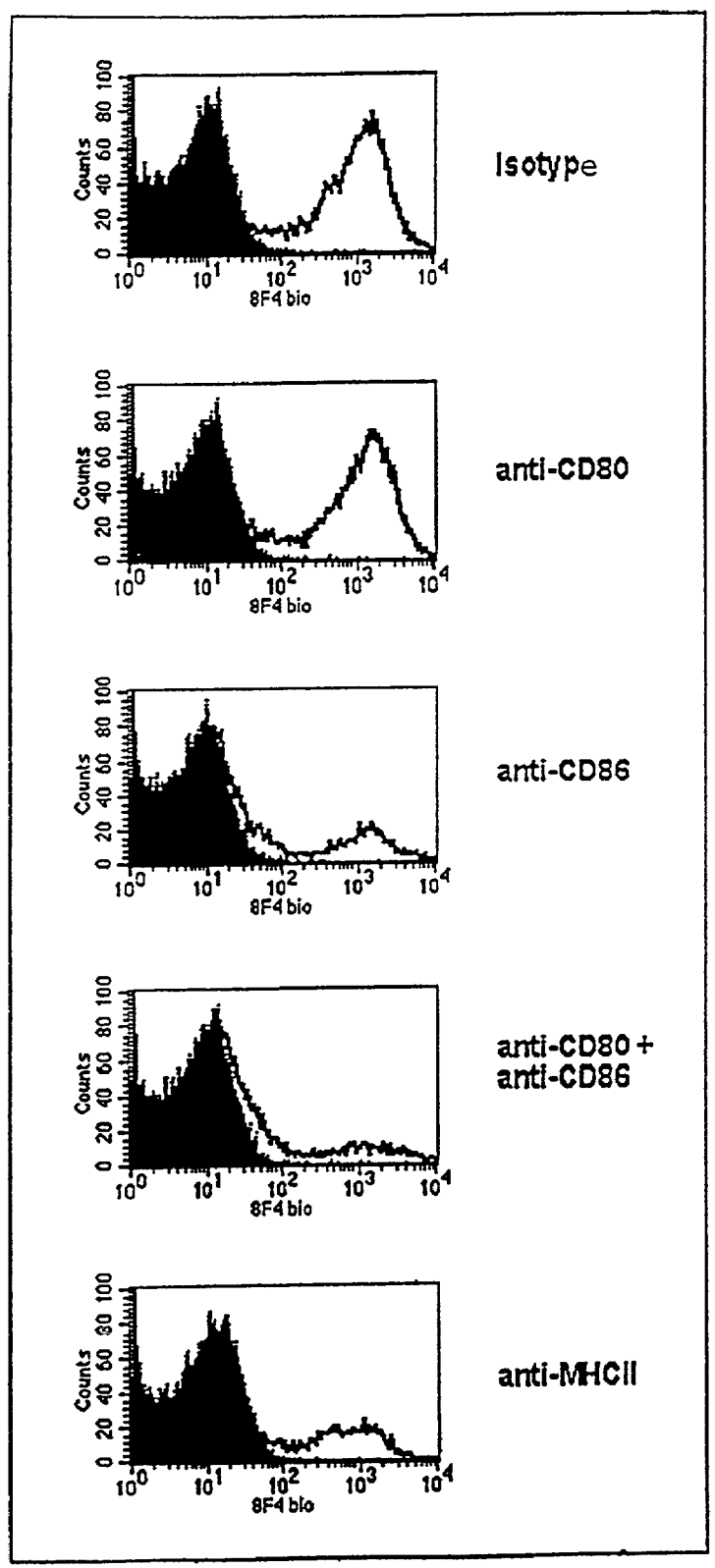
FIG. 3 shows the result of a flow cytometry for identifying molecules which are involved in the induction of 8F4 in the mixed lymphocyte reaction. "bio" means biotinylated antibody.
Figure 4:
FIG. 4 shows the result of a histochemical investigation for localization of 8F4-positive cells in the tonsil.
Figure 5:
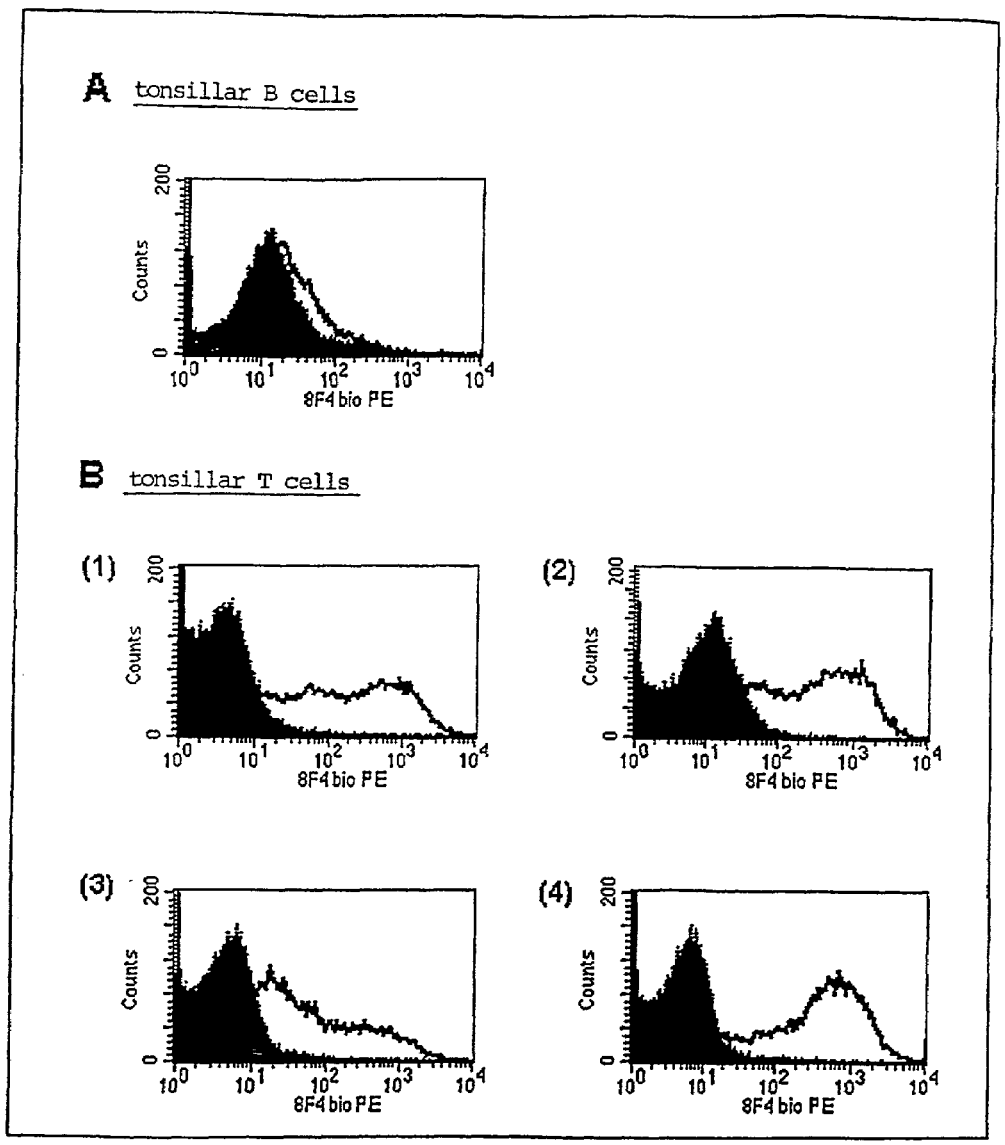
FIG. 5 shows the result of an expression analysis of 8F4 on T and B cells from human tonsils in a flow cytometry.
Figure 12:
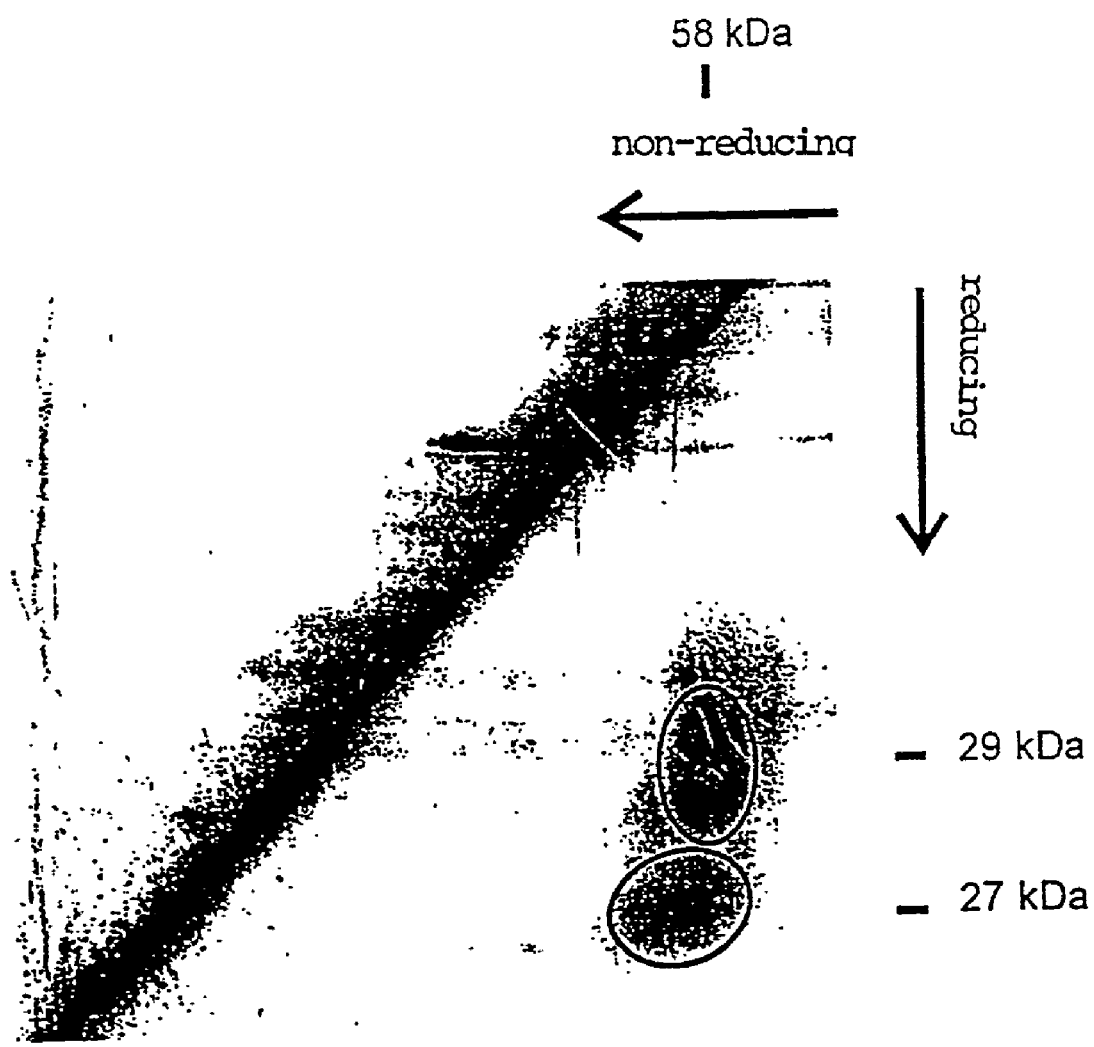

FIG. 12 shows the two-dimensional gel electrophoresis. A MOLT-4V cell lysate from 300×10$^6$ cells was immunoprecipitated as described. The eluate was fractionated on a non-reducing SDS-PAGE (10% PAA), and the region around 60 kDa was cut out of the gel. To reduce the disulphide bridges in the 8F4 molecule, the piece of gel was incubated in 5.3 M urea, 0.5 M Tris, pH 8.0, 1% SDS, 1% β-mercaptoethanol at 50° C. for 1 h, and the free cysteine residues in the molecule were alkylated with 10 mM iodoacetamide (Sigma, Deisenhofen) (37° C., 30 min). The piece of gel was equilibrated in 1×SDS-PAGE sample buffer for a further 30 min and mounted on a 12% PAA-SDS gel (with stacking gel). After fractionation by electrophoresis, the gel underwent silver staining. The location of the 8F4 protein was determined by surface iodination (cf. FIG. 1) and is marked by a circle. (All the procedures not described in detail were carried out by standard methods, see, for example, Westermeier, R., Electrophoresis in Practice, VCH Verlagsgesellschaft, Weinheim, 1997).

Figure 13:
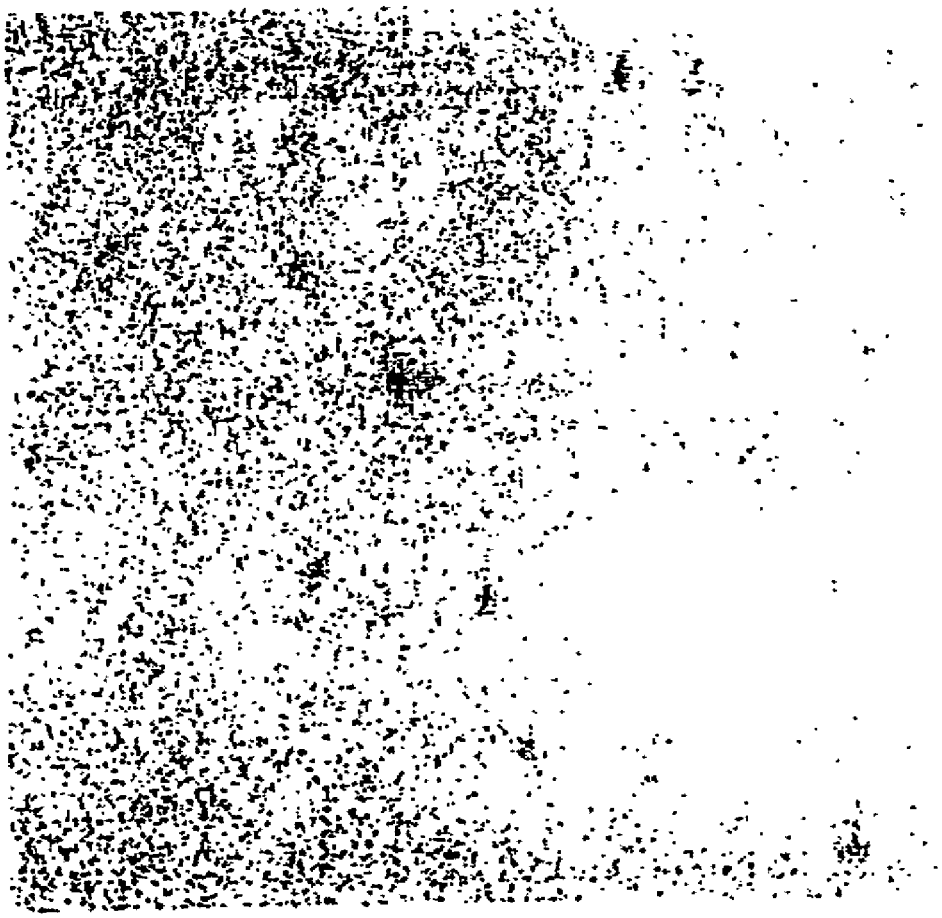

FIG. 13 shows a hybridization with Oligo 1 (SEQ ID NO:3). Lambda clones immobilized on nitrocellulose filters were hybridized with Oligo 1 as described in the examples. Exposure on an X-ray film is depicted (detail)

Figure 14:
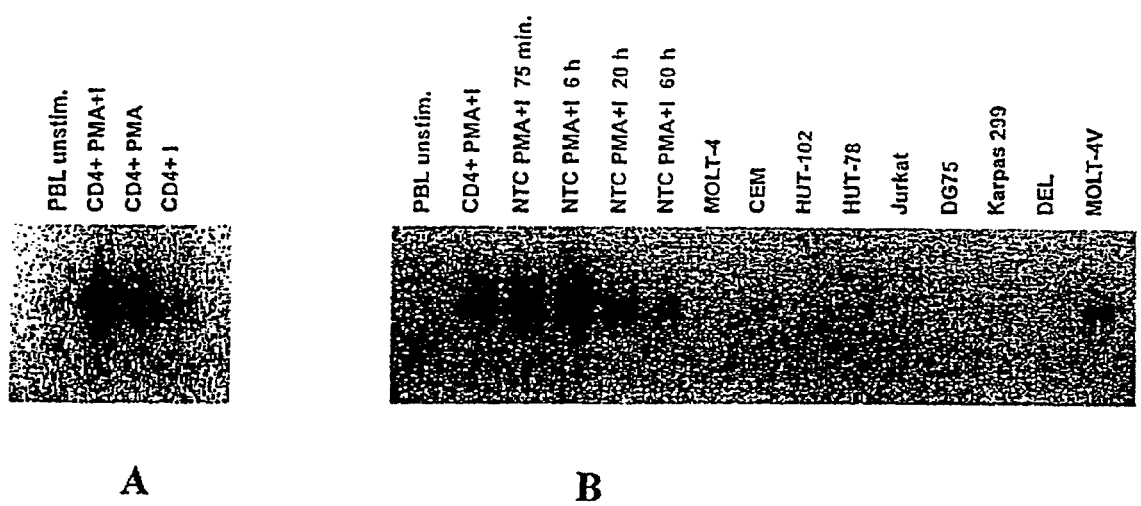

FIG. 14 shows a Northern blot analysis with the 8F4 cDNA. Hybridization of a Northern blot with the 8F4 cDNA produces a band which migrates in the gel between the 18S and 28S RNA. FIG. 14A shows the behaviour as 2-signal-dependent (see above) activation antigen: no expression in resting lymphoid cells (PBL), strong expression in PMA+ionomycin-activated CD4$^+$ T cells and distinctly reduced expression with PMA or ionomycin alone. FIG. 14B shows the strength of mRNA expression after different stimulation times (T cells (purified via nylon wool adherence, NTC), stimulated with PMA+ionomycin). Besides this the MOLT-4 cell lines (ATCC CRL-1582) which shows only minimal expression, and on the far right the MOLT-4V which was used for the cloning and which shows a distinct signal. Also loaded is the RNA from other cell lines on which no 8F4 expression was detectable in the analysis by flow cytometry: CEM (ATCC CCL-119), HUT-102 (ATCC TIB-162), HUT-78 (ATCC TIB-161), Jurkat (ATCC TIB-152), DG75 (Deutsche Sammlung von Mikroorganismen und Zellkulturen (DSMZ) ACCS3), Karpas 299 (Fischer, P. et al. (1988), Blood, 72:234–240), DEL (Barbey, S. et al. (1990), Int. J. Cancer, 45:546–553).

FIG. 15 shows the amino acid sequence of the polypeptide 8F4 (SEQ ID NO:2).

FIG. 16 shows the 8F4 cDNA (SEQ ID NO:1).

The following examples illustrate the invention and are not to be understood restrictively.

EXAMPLE 1

Generation of the 8F4 Antibody

Balb/c mice were immunized with human T cells which had previously been activated for 24 h with 33 ng/ml of the phorbol ester phorbol myristate acetate (PMA) (Sigma, Deisenhofen) and with 200 ng/ml of the Ca$^{2+}$ ionophore ionomycin (Sigma, Deisenhofen) (so-called "2-signal activation"). After boosting three times, the spleen cells of the mice were fused with the myeloma P3X63Ag8.653 (ATCC No. CRL-1580), and antibody secreting hybridomas were generated by standard methods; cf. Peters and Baumgarten, Monoclonal Antibodies, Springer, Heidelberg, 1992. The resulting antibodies were screened for activated versus resting T cells in flow cytometry. Activated ("2-signal activation") and resting T cells were incubated with the hybridoma supernatant and then labelled with a fluorescence-labelled secondary antibody; cf. Shapiro, Practical Flow Cytometry, Wiley-Liss, New York, 1995. Only the antibodies which recognize molecules which were induced exclusively by PMA and the Ca$^{2+}$ ionophore ionomycin on the T-cell surface, but not by one of the agents alone ("2-signal molecules"), were selected for further purification. The resulting antibodies were investigated in flow cytometry for similarity to or difference from known antibodies against activation molecules (cf. Table 1) on T cells. The criteria for this were, besides the abovementioned "2-signal dependence", the kinetics of induction on stimulated T cells and the expression on various cell lines.

EXAMPLE 2

Immunoprecipitation of the 8F4 Antigen

Surface molecules from activated human T cells were iodinated with $^{125}$I by standard methods and immunoprecipitated with the antibody 8F4 by standard methods; cf. Goding, Monoclonal Antibodies: Principle and Practice, Academic Press, London, 1996. The antibody for the immunoprecipitation was coupled by the method of Schneider et al., *Journal of Biological Chemistry* 257 (1982), 10766–10769, to protein G (Pharmacia, Freiburg) (8F4 matrix). The matrix was washed as described by Schneider et al., see above. The immunoprecipitated 8F4 molecule was analyzed for its molecular mass in an SDS-PAGE (non-reduced and reduced) in a conventional way; Goding, see above.

EXAMPLE 3

Flow Cytometry

The 8F4-carrying T cells were analysed in flow cytometry by standard methods; cf. Shapiro, Practical Flow Cytometry, Wiley-Liss, New York, 1995.

Exemplary Embodiment 3.1: Flow Cytometry After Induction of the 8F4 Antigen on CD4+ T Cells.

CD4+ T cells from peripheral blood were stimulated with various agents in a conventional way, and investigated for expression of the 8F4 molecule in flow cytometry by a conventional method. The activation time for the T cells was between 24 hours and 144 hours with the various agents. Modes of activation: phorbol myristate acetate (PMA; 33 ng/ml), ionomycin (200 ng/ml), phytohaemagglutinin (PHA 1.5 mg/ml), OKT3 (monoclonal antibody against CD3), mixed lymphocyte reaction (MLR, between 50,000 CD4+ T cells and 100,000 B cells), mAk 9.3 (monoclonal antibody against CD28), staphylococcal enterotoxin B (SEB, 0.1 ng/ml). Analysis revealed that various stimuli are suitable for inducing the 8F4 molecule on T cells, but the expression density differs. The most potent stimuli, besides the highly active pharmacological agents PMA and ionomycin, are those which represent a costimulatory situation such as, for example, accessory cells in the MLR or the costimulating mAk 9.3.

Exemplary Embodiment 3.2: Kinetics of Induction of the 8F4 Antigen on CD4+ T Cells After Activation with PMA, and Ionomycin.

CD4− T cells from peripheral blood were stimulated with PMA (33 ng/ml) and ionomycin (200 ng/ml) in a conventional way and investigated after 0, 4, 8, 12, 24 and 48 hours for expression of the 8F4 molecule by flow cytometry in a conventional way. The molecule is detectable on the surface after only four hours, and thus belongs to the class of relatively early activation antigens. There is still good expression of the antigen even after 48 hours.

Exemplary Embodiment 3.3: Flow Cytometry to Identify Molecules Which are Involved in the Induction of 8F4 in the "Mixed Lymphocyte Reaction".

50,000 CD4+ T cells from peripheral blood were co-cultivated with 100,000 allogeneic tonsillar B cells for 6 days (37° C., 5.2% $CO_2$, 200 μl of RPMI 1640 with 10% FCS in 96-well round-bottom plates) and then investigated for expression of the 8F4 molecule in flow cytometry. At the start of cultivation, various antibodies (anti-CD80, anti-CD86, anti-MHCII; all 10 mg/ml) were added to the culture in order to examine the dependence of 8F4 induction on these molecules. Expression of 8F4 can be blocked only by blockade of the CD86/CD28 interaction, but not by blockade of CD80. The blockade effect in this case is even stronger than the blockade of MHCII (positive control).

Exemplary Embodiment 3.4: Expression of 8F4 on T and B Cells from Human Tonsils.

B cells and T cells from tonsillar tissue from various sources were purified in a conventional way and investigated by flow cytometry for expression of the 8F4 molecule. Whereas the signal was not unambiguously significant on B cells, there was expression of the 8F4 molecule in varying density by about 50–80% of tonsillar T cells. It is possible in this case to identify two populations differing in the level of fluorescence (8F4 high and low, respectively), and differing in expression on the various tonsils. Thus, for example, tonsils show a pronounced 8F4 low population and other tonsils show a pronounced 8F4 high population.

Exemplary Embodiment 3.5: Coexpression of the 8F4 Molecule with Other Activation Markers.

T cells purified from human tonsils were analysed in 2-colour flow cytometry for coexpression of the 8F4 molecule with other activation markers. In tonsils, 8F4 is coexpressed with CD69 as well as with variants of the CD45 molecule. In this case, the 8F4 high cells are unambiguously correlated with a CD45R0 expression, while the 8F4-negative cells carry the phenotype CD45RA. CD45RA is mainly expressed by so-called "naive" T cells, whereas CD45RO is associated with an effector cell function. The 8F4+ cells are thus mainly "mature" T cells. CD45RO and CD45RA are isoforms of CD45.

EXAMPLE 4

Localization of 8F4-positive Cells in the Tonsil

Tonsillar tissue in frozen sections was stained with the 8F4 antibody in the APAAP technique (alkaline phosphatase-anti-alkaline phosphatase) by standard methods. 8F4+ cells were found preferentially in the germinal centre of the tonsils, but also in part in the T-cell zone of the tonsils.

EXAMPLE 5

Costimulation of T Lymphocytes 96-well plates were coated with a goat anti-mouse Ig antibody (20 μg/ml), washed, and loaded with the anti-CD3 monoclonal antibody OKT3 (various dilutions of an ascites) and the 8F4 antibody according to the invention (2 μg/ml). The OKM1 antibody or the 2A11 antibody (both 2 μg/ml) were used as isotype control.

Exemplary Embodiment 5.1: Enhanced Expression of Activation Molecules on T Lymphocytes After Costimulation by 8F4.

Purified CD4+ T cells from peripheral blood were activated with various concentrations of the monoclonal antibody OKT3 and, at the same time, costimulated with the 8F4 antibody or a nonspecific antibody of the same isotype. As comparison, costimulation was carried out with the anti-CD28 antibody-9.3, one of the strongest known costimulatory antibodies. Even with optimal stimulation by CD3, a costimulatory effect is still to be seen both with the mAk 8F4 and with the mAk 9.3. In the suboptimal OKT3 region, that is to say the region in which complete T-cell activation cannot be achieved without costimulation, both antibodies are able to increase the expression of other activation antigens by a factor of 4 to 100, and the effect of the anti-CD28 antibody is still visible even at very high OKT3 dilutions. This is attributable to the fact that with very weak OKT3 stimulation the 8F4 antigen is no longer brought to the cell surface and thus cannot be crosslinked by the mAk 8F4 either.

Exemplary Embodiment 5.2: Comparison of the Costimulating Effect of 8F4 with the. Costimulating Effect of CD2 S.

Purified CD8+ T cells were stimulated with a suboptimal concentration of the monoclonal antibody OKT3 for 51 h. The costimulators employed were antibody 8F4, antibody 9.3 (anti-CD28) and isotype controls (2 μg/ml each). After completion of the stimulation time, the T-cell proliferation rate was determined by $^3$H-thymidine incorporation. In parallel cultures, the supernatant was removed and the concentration of the cytokines ATAC/lymphotactin and IL-2 was determined. 8F4 and CD28 differ greatly from one another in relation to IL-2 synthesis. CD28 costimulation leads, as also described in the prior art (Chambers and Allison, *Current Opinion in Immunology* 9 (1997), 396–404), to very extensive IL-2 secretion. By contrast, IL-2 production with 8F4 is below the detection limit. However, proliferation is comparable in the two mixtures, and thus the autocrine growth of the T cells must be attributed to other factors on costimulation of 8F4. The two antibodies also differ scarcely at all in the costimulatory effect in relation to secretion of the lymphokine ATAC.

EXAMPLE 6

Determination of the Immunoglobulins Synthesized by B Cells After Interaction with 8F4-costimulated T Cells 96-well plates were coated with a goat anti-mouse Ig antibody (20 μg/ml), and loaded with the antiCD3 monoclonal antibody OKT 3 (1:500 to 1:80,000 ascites) and the 8F4 antibody according to the invention (2 μg/ml). The OKM1 antibody or the 2A11 antibody was used as isotype control. In some experiments, a costimulation was carried out with a CD28-specific antibody ("9.3") for comparison; cf. Hara et al., *Journal of Experimental Medicine* 161 (1985), 1513–1524. 50,000 purified (Magnetobeads, Dynal, Hamburg) $CD4^+$ T cells (>95% purity) from peripheral blood and 25,000 allogenic tonsillar B cells (negative selection by T-cell rosetting with sheep erythrocytes, 96% purity) were pipetted into each well of the culture plates pretreated in this way, and cocultivated for 5 days. After this period, the supernatant was removed and analysed for the concentration of secrete immunoglobulins of the IgM and IgG types in an ELISA in a conventional way; cf. Nishioka and Lipsky, *Journal of Immunology* 153 (1994), 1027–1036.

Exemplary Embodiment 6.1: Enhancement of the Synthesis of Antibodies of the IgM and IgG Types by the B Cells After Costimulation of T Cells.

Purified $CD4^+$ T cells from peripheral blood were cocultivated with allogeneic B cells from tonsils for 8 days in a conventional way. With suboptimal stimulation of the T cells with the OKT3 antibody, the costimulation of the T cells by 8F4 enhances the secretion of IgM and IgG immunoglobulins by a factor of 40.

EXAMPLE 7

Prevention of the Activation-induced Apoptosis of Peripheral T Cells After Costimulation by 8F4.

Peripheral T cells (purified by nylon wool adherence in a conventional way), were stimulated with PHA (1.5 mg/ml) for 20 h and cultivated with IL-2 for 6 days. The cells were then restimulated by OKT3 with and without costimulation by mAk 8F4 (2 μg/ml). The apoptosis was determined by staining the DNA with propidium iodide in flow cytometry (FACS). With suboptimal stimulation via the T-cell receptor complex, costimulation by 8F4 can reduce the proportion of apoptotic cells by a factor of 4.

EXAMPLE 8

Cloning of the cDNA Coding for the 8F4 Protein

A cell line (MOLT-4V) which expresses the 8F4 antigen constitutively was identified in flow cytometry by staining with a fluorescent dye-coupled 8F4 antibody (FIG. 11). The MOLT-4V line is a variant of the human T-cell line MOLT-4 (American Type Culture Collection (ATCC) CRL-1582).

This cell line was used for preparative purification of the 8F4 antigen with the aid of the monoclonal antibody:

The cells were, cultivated on a large scale (150 l) in roller culture bottles and removed by centrifugation, and the cellular proteins were extracted using a lysis buffer (50 mM Tris, pH 8.0, 150 mM NaCl, 1 mM EDTA, 1 mM PMSF (Sigma, Deisenhofen), 1% NP-40 (Boehringer, Mannheim)). Cell nuclei and other insoluble constituents were removed by ultracentrifugation. The cell lysate obtained in this way was preincubated with Sepharose CL4-B (Pharmacia, Freiburg) for 2 h in order to remove proteins which bind nonspecifically to Sepharose. Incubation then took place with the 8F4 immunoaffinity matrix described in Example 2 above (4 h at 4° C.). The matrix was packed into a column and then washed several times under conditions with which there is exclusive removal of nonspecifically binding proteins (1.50 mM Tris, pH 8.0, 300 mM NaCl, 1 mM EDTA, 1 mM PMSF, 0.5% NP-40; 2.50 mM Tris, pH 8.0, 150 mM NaCl, 1 mM EDTA, 1 mM PMSF, 0.5% NP-40, 0.1% SDS; 3.0.2 M glycine pH 4.0, 0.5% CHAPS (Merck, Darmstadt)). The 8F4 antigen was eluted from the matrix with 0.2 M glycine, pH 2.5, 0.5% CHAPS. The eluate was concentrated by ultrafiltration (Amicon Centricon 10, Millipore, Eschborn)

In order to achieve further purification of the 8F4 molecule, the dimeric structure of the molecule (see FIG. 1) was utilized in a two-dimensional gel electrophoresis (nonreducing/reducing): since most proteins occur as monomer, they migrate on a diagonal in gel electrophoresis, whereas the 8F4 molecule migrates at 55–60 kDa in the 1st dimension (nonreducing) and at 27 and 29 kDa (FIG. 12) in the 2nd dimension (reducing).

For preparative fractionation, the immunoprecipitates from in each case $20 \times 10^9$ cells were prepared as described above for FIG. 12 and fractionated in two-dimensional gel electrophoresis, the gel was stained with Coomassie blue G250 (Biorad, Munich) and the areas indicated in FIG. 12 were separately cut out of the gel (8F4-27 kDa and 8F4-29 kDa respectively).

For peptide microsequencing, the proteins from in each case 4 pieces of gel were digested with trypsin and eluted from the gel. The tryptic fragments were fractionated by HPLC and individual fractions were subjected to Edman degradation (method described in detail in Groettrup, M. et al. (1996), Eur. J. Immunol., 26:863–869)

Sequencing of the 8F4-29 kDa sample revealed, besides fragments of known proteins, a peptide sequence XRLTDVT for which no human correlate was found in any of the protein databases.

Unambiguous translation back of a protein sequence into a DNA sequence is not possible. Thus, translation of the above peptide sequence back into an oligonucleotide with 17 nucleotides results in 2048 permutations. However, a specific method (Wozney, J. M. (1990), Methods Enzymol. 182:738–751) makes it possible to screen a cDNA bank with degenate oligonucleotides. On the basis of the peptide sequence found, 2 oligonucleotides (Oligo 1 (SEQ ID NO:3); MGN CTS ACN GAY GTN AC, 512 permutations; Oligo 2 (SEQ ID NO:4): MGN YTD ACN GAY GTN AC, 1024 permutations) were synthesized.

For screening, a cDNA bank was constructed from the MOLT-4V cell line also used for the protein purification:

Complete RNA was isolated by the guanidinium/CsCl method (Chirgwin, J. M. et al. (1979), Biochemistry 18:5294–5299), and mRNA was concentrated on Oligo-dT-cellulose columns (Gibco BRL, Eggenstein). Synthesis of the first and second cDNA strands was carried out using a commercial cDNA synthesis system (Gibco BRL, Eggenstein) using Oligo-dT primers in accordance with the manufacturer's instructions. The cDNA was ligated via EcoRI adaptors into the Lambda ZAPII vector (Stratagene, Heidelberg).

The cDNA bank was plated out by standard methods (Vogeli, G. and Kaytes, P. S. (1987), Methods Enzymol., 152:407–515) and the Lambda DNA was immobilized on nitrocellulose filters (Optitran BA-S 85, Schleicher & Schuell, Dassel).

The abovementioned oligonucleotides were radiolabelled using T4 polynucleotide kinase (NEBL, Schwalbach) and γ-$^{32}$P ATP (NEN Du Pont, Brussels) (Wallace, R, B. and Miyada, C. G. (1987), Methods Enzymol., 152:432–442).

Hybridization of the filters took place in a buffer described for degenerate oligonucleotides (Wozney, J. M. (1990), Methods Enzymol. 182:738–751) with 3 M tetramethylammonium chloride (Roth, Karlsruhe) at 48° C. The filters were washed as described in the abovementioned reference, the washing temperature being 50° C. Exposure of these filters on an X-ray film revealed about 50 positive clones per 100,000 plated phages (FIG. 13).

6 clones were further characterized by transferring them by in vivo excision, using the method described by the manufacturer of the vector (Stratagene, Heidelberg), into a plasmid vector, and partially sequencing with T3 and T7 primers (BigDye Terminator Cycle Sequencing Kit, Applied Biosystems, Foster City, USA). One of the clones contained a sequence which on translation provided exactly the peptide sequence which was sought. This clone was used for hybridization of a Northern blot (FIG. 14) (Kroczek, R. A. (1993), J. Chromatogr., 618, 133–145). The expression pattern of the mRNA corresponded exactly to the expression of the 8F4 molecule as was known from investigations on the monoclonal antibody by flow cytometry. Since the clone which was found contained only the 3' end of the cDNA sought, a fragment on the 5' side was used to isolate the complete 8F4 cDNA. Several clones were sequenced on both strands.

The 8F4 cDNA (2641 nucleotides) is depicted in FIG. 16 and in the sequence listing under SEQ ID NO:1, and codes for a protein having 199 amino acids (Nucleotides 68–664), depicted in FIG. 15 and in the sequence listing under SEQ ID NO:2. Sequencing of several independent clones from the cDNA bank showed some deviations from the sequence shown here, but these are all in the 3'-untranslated region:

Pos. 909–910:deletion
Pos. 1631:T->C
Pos. 2074:G->T
Pos. 2440:G->C
Pos. 2633: alternative polyadenylation site Table 1

Table 1 summarizes the antibodies used (clone), their source of origin (source), the specificity for their particular antigen (specificity) and, where appropriate, their labelling (label).

| Specificity | Label | Isotype | Clone | Source |
| --- | --- | --- | --- | --- |
| CD3 | Cy-Chrome | IgG1 | UCHT1 | Pharmingen, Hamburg |

| Specificity | Label | Isotype | Clone | Source |
| --- | --- | --- | --- | --- |
| CD3 | — | IgG2a | OKT3 | ATCC CRL-8001 |
| CD11b | — | IgG2b | OKM1 | ATCC CRL-8026 |
| CD25 | FITC | IgG2a | B1.49.9 | Immunotech, Hamburg |
| CD28 | — | IgG2a | 9.3 | Immunex Corp., Seattle |
| CD45RA | Cy-Chrome | IgG2b | HI100 | Pharmingen, Hamburg |
| CD45RO | FITC | IgG2a | UCHL1 | Immunotech, Hamburg |
| CD69 | FITC | IgG1 | FN50 | Pharmingen, Hamburg |
| CD80 | — | IgG1 | L307.4 | Becton Dickinson, Heidelberg |
| CD86 | — | IgG2b | IT2.2 | Pharmingen, Hamburg |
| CD154 | FITC | IgG1 | TRAP-1 | Hybridoma[1] |
| MHCII | — | IgG2a | L243 | ATCC HB-55 |
| 8F4 | — | IgG1 | 8F4 | Hybridoma[1] |
| 8F4 | Biotin | IgG1 | 8F4 | Hybridoma[1] |
| Isotype IgG1 | — | IgG1 | 2A11 | Hybridoma[1,2] |
| Isotype IgG1 | FITC | IgG1 | 2A11 | Hybridoma[1,2] |
| Isotype IgG1 | Biotin | IgG1 | ASA-1 | Hybridoma[1] |

[1]The hybridoma cell line was generated in a conventional way, and the antibody was purified and labelled where appropriate.
[2]Directed against a synthetic peptide The antisera and secondary reagents used in the examples were purchased from: goat anti-mouse Ig, FITC conjugated, from Jackson Immuno Research Lab., USA; Streptavidin, PE-conjugated, from Jackson Immuno Research Lab., USA; rabbit anti-mouse Ig fraction, from Sigma, Deisenhofen.

It will be apparent to those skilled in the art that various modifications and variations can be made to the compositions and processes of this invention. Thus, it is intended that the present invention cover such modifications and variations, provided they come within the scope of the appended claims and their equivalents.

Priority applications DE 19741929.1 filed Sep. 23, 1997 and DE 19821060.4 filed May 11, 1998 including the specification, drawings, claims and abstract, are hereby incorporated by reference. All publications cited herein are incorporated in their entireties by reference.

DEPOSIT OF HYBRIDOMA

The hybridoma 8F4, secreting native monoclonal antibody 8F4, was deposited with the Deutsche Sammlung Von Mikroorganismen und ZellKulturen GmbH ("DSMZ"), at Mascheroder Weg 1b, D-3300 Braunschweig, Germany, on Apr. 9, 2002, in compliance with the Budapest Treaty on the International Recognition of the Deposit of Microorganisms for the Purposes of Patent Procedure on behalf of the Applicant and the Robert-Koch-Institut. The deposited hybridoma was assigned DSMZ accession number DSM ACC2539.

The invention claimed is:

1. A method for treating an asthmatic disorder, comprising:

administering to an individual in need of treatment an 8F4 inhibitory molecule, wherein said 8F4 inhibitory molecule is a monoclonal antibody that recognizes a human 8F4 polypeptide, wherein said 8F4 polypeptide:

a) is an inducible T cell costimulatory molecule:

b) occurs on two-signal-activated human CD4$^+$ T lymphocytes from human peripheral blood;

c) exhibits a molecular weight of about 55 to 60 kilodaltons as determined by non-reducing sodium dodecyl sulphate polyacrylamide gel electrophoresis (SDS-PAGE); and d) is a dimer of two peptide chains exhibiting molecular weights of about 27 kilodaltons and 29 kilodaltons, as measured by reducing SDS-PAGE, wherein the human 8F4 polypeptide is recognized by the antibody produced by the hybridoma deposited with the Deutsche Sammlung von Mikroorganismen und Zellkulturen GmbH ("DSMZ") and assigned accession no. DSM ACC2539:

and wherein the monoclonal antibody, in conjunction with anti-CD3 monoclonal antibody OKT3, costimulates proliferation of human T lymphocytes under conditions in which the monoclonal antibody and OKT3 are immobilized on an anti-mouse Ig-coated 96 well plate;

in an amount sufficient to ameliorate a symptom of the asthmatic disorder, such that the asthmatic disorder is treated.

2. The method of claim 1, wherein the monoclonal antibody recognizes the human 8F4 polypeptide of about 55 kilodaltons to 60 kilodaltons, as determined by non-reducing SDS-PAGE.

3. The method of claim 1, wherein the monoclonal antibody recognizes the peptide chain of about 27 kilodaltons, as determined by reducing SDS-PAGE.

4. The method of claim 1, wherein the monoclonal antibody recognizes the peptide chain of about 29 kilodaltons, as determined by reducing SDS-PAGE.

5. The method of claim 1, wherein the monoclonal antibody recognizes a human 8F4 polypeptide present on activated human CD4$^+$ T lymphocytes and activated human CD8$^+$ T lymphocytes.

* * * * *

SEQUENCE LISTING

<160> NUMBER OF SEQ ID NOS: 4

<210> SEQ ID NO 1
<211> LENGTH: 2641
<212> TYPE: DNA
<213> ORGANISM: 8F4

<400> SEQUENCE: 1

```
cgagagcctg aattcactgt cagctttgaa cactgaacgc gaggactgtt aactgtttct      60
ggcaaacatg aagtcaggcc tctggtattt ctttctcttc tgcttgcgca ttaaagtttt     120
aacaggagaa atcaatggtt ctgccaatta tgagatgttt atatttcaca acggaggtgt     180
acaaatttta tgcaaatatc ctgacattgt ccagcaattt aaaatgcagt tgctgaaagg     240
ggggcaaata ctctgcgatc tcactaagac aaaaggaagt ggaaacacag tgtccattaa     300
gagtctgaaa ttctgccatt ctcagttatc caacaacagt gtctcttttt ttctatacaa     360
cttggaccat tctcatgcca actattactt ctgcaaccta tcaattttg atcctcctcc      420 ttttaaagta actcttacag gaggatattt gcatatttat gaatcacaac tttgttgcca     480
gctgaagttc tggttaccca taggatgtgc agcctttgtt gtagtctgca tttgggatg      540 catacttatt tgttggctta caaaaaagaa gtattcatcc agtgtgcacg accctaacgg     600
tgaatacatg ttcatgagag cagtgaacac agccaaaaaa tctagactca cagatgtgac     660
cctataatat ggaactctgg cacccaggca tgaagcacgt tggccagttt cctcaacttt    720
gaagtgcaag attctcttat ttccgggacc acggagagtc tgacttaact acatacatct     780
tctgctggtg ttttgttcaa tctggaagaa tgactgtatc agtcaatggg gattttaaca    840
gactgccttg gtactgccga gtcctctcaa aacaaacacc ctcttgcaac cagctttgga     900
gaaagcccag ctcctgtgtg ctcactggga gtggaatccc tgtctccaca tctgctccta     960
gcagtgcatc agccagtaaa acaaacacat ttacaagaaa atgttttaa agatgccagg    1020 ggtactgaat ctgcaaagca aatgagcagc caaggaccag catctgtccg catttcacta    1080
tcatactacc tcttctttct gtagggatga gaattcctct tttaatcagt caagggagat    1140
gcttcaaagc tggagctatt ttatttctga gatgttgatg tgaactgtac attagtacat    1200
actcagtact ctccttcaat tgctgaaccc cagttgacca ttttaccaag actttagatg    1260 cttttcttgtg ccctcaattt tcttttaaa aatacttcta catgactgct tgacagccca    1320
acagccactc tcaatagaga gctatgtctt acattctttc ctctgctgct caatagtttt    1380
atatatctat gcatacatat atacacacat atgtatataa aattcataat gaatatattt    1440
gcctatattc tccctacaag aatatttttg ctccagaaag acatgttctt ttctcaaatt    1500
cagttaaaat ggtttacttt gttcaagtta gtggtaggaa acattgcccg gaattgaaag    1560
caaatttatt ttattatcct attttctacc attatctatg ttttcatggt gctattaatt    1620
acaagtttag ttcttttttgt agatcatatt aaaattgcaa acaaaatcat ctttaatggg    1680
ccagcattct catggggtag agcagaatat tcatttagcc tgaaagctgc agttactata    1740
ggttgctgtc agactatacc catggtgcct ctgggcttga caggtcaaaa tggtccccat    1800
cagcctggag cagccctcca gacctgggtg gaattccagg gttgagagac tcccctgagc    1860
cagaggccac taggtattct tgctcccaga ggctgaagtc accctgggaa tcacagtggt    1920
ctacctgcat tcataattcc aggatctgtg aagagcacat atgtgtcagg cacaattcc     1980 ctctcataaa aaccacacag cctggaaatt ggccctggcc cttcaagata gccttcttta    2040
gaatatgatt tggctagaaa gattcttaaa tatgtggaat atgattattc ttagctggaa    2100
tattttctct acttcctgtc tgcatgccca aggcttctga agcagccaat gtcgatgcaa    2160
caacatttgt aactttaggt aaactgggat tatgttgtag tttaacattt tgtaactgtg    2220
tgcttatagt ttacaagtga gacccgatat gtcattatgc atacttatat tatcttaagc    2280
atgtgtaatg ctggatgtgt acagtacagt actgaacttg taatttgaat ctagtatggt    2340
```

```
gttctgtttt cagctgactt ggacaacctg actggctttg cacaggtgtt ccctgagttg    2400
tttgcaggtt tctgtgtgtg gggtggggta tggggaggag aaccttcatg gtggcccacc    2460
tggcctggtt gtccaagctg tgcctcgaca catcctcatc cccagcatgg acacctcaa     2520 gatgaataat aattcacaaa atttctgtga aatcaaatcc agttttaaga ggagccactt    2580
atcaaagaga ttttaacagt agtaagaagg caaagaataa acatttgata ttcagcaact    2640
g                                                                   2641
```

<210> SEQ ID NO 2
<211> LENGTH: 198
<212> TYPE: PRT
<213> ORGANISM: 8F4

<400> SEQUENCE: 2

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu Ile
145                 150                 155                 160

Cys Trp Leu Thr Lys Lys Lys Tyr Ser Ser Ser Val His Asp Pro Asn
                165                 170                 175

Gly Glu Tyr Met Phe Met Arg Ala Val Asn Thr Ala Lys Lys Ser Arg
            180                 185                 190

Leu Thr Asp Val Thr Leu
        195
```

<210> SEQ ID NO 3
<211> LENGTH: 17
<212> TYPE: PRT
<213> ORGANISM: 8F4

<400> SEQUENCE: 3

```
Met Gly Asn Cys Thr Ser Ala Cys Asn Gly Ala Tyr Gly Thr Asn Ala
1               5                   10                  15

Cys
```

<210> SEQ ID NO 4
<211> LENGTH: 17
<212> TYPE: PRT
<213> ORGANISM: 8F4

-continued

```
<400> SEQUENCE: 4

Met Gly Asn Tyr Thr Asp Ala Cys Asn Gly Ala Tyr Gly Thr Asn Ala
1               5                   10                  15
Cys
```